(12) United States Patent
De Baets et al.

(10) Patent No.: US 12,129,261 B2
(45) Date of Patent: Oct. 29, 2024

(54) CRYSTALLINE FORMS OF A MCL-1 INHIBITOR, A PROCESS FOR THEIR PREPARATION AND PHARMACEUTICAL COMPOSITIONS CONTAINING THEM

(71) Applicants: LES LABORATOIRES SERVIER, Suresnes (FR); VERNALIS (R&D) LTD, Cambridge (GB)

(72) Inventors: Emilie De Baets, Notre Dame de Bondeville (FR); Julien Auvray, Honfleur (FR); Michael Lynch, Saint Jean de la Ruelle (FR); Nicolas Leblanc, Lion-en-Beauce (FR)

(73) Assignees: LES LABORATOIRES SERVIER, Suresnes (FR); VERNALIS (R&D) LTD, Cambridge (GB)

( * ) Notice: Subject to any disclaimer, the term of this patent is extended or adjusted under 35 U.S.C. 154(b) by 741 days.

(21) Appl. No.: 17/295,521

(22) PCT Filed: Dec. 5, 2019

(86) PCT No.: PCT/EP2019/083773
§ 371 (c)(1),
(2) Date: May 20, 2021

(87) PCT Pub. No.: WO2020/115183
PCT Pub. Date: Jun. 11, 2020

(65) Prior Publication Data
US 2022/0017533 A1  Jan. 20, 2022

(30) Foreign Application Priority Data
Dec. 6, 2018 (EP) .................................... 18306634

(51) Int. Cl.
*C07D 495/04* (2006.01)
(52) U.S. Cl.
CPC ........ *C07D 495/04* (2013.01); *C07B 2200/13* (2013.01)
(58) Field of Classification Search
CPC ........ A61P 35/00; A61P 37/00; A61K 31/519; A61K 45/06; C07D 495/04
See application file for complete search history.

(56) References Cited

FOREIGN PATENT DOCUMENTS

WO    WO2015097123    7/2015
WO    WO2016207225    12/2016
WO    WO-2016207225 A1 * 12/2016 ........... A61K 31/519

OTHER PUBLICATIONS

He. Blood, Feb. 2007. vol. 109, No. 4 (Year: 2007).*
Xiang. Onco Targets and Therapy 2018:11 7301-7314 (Year: 2018).*
Empyrean Trademark of Empyrean International, LLC. Trademark (Year: 2024).*
Panalytical Trademark of Malvern Panalytical B.V. (Year: 2024).*
PIXCEL1D Trademark of PANalytical B.V. (Year: 2024).*
Caira, Mino, R., "Crystalline polymorphism of organic compounds", Topics in Current Chemistry, vol. 198, Jan. 1, 1998, pp. 163-208.
Internatonal Search Report for PCT/EP2019/083773 dated Jan. 20, 2020.

* cited by examiner

*Primary Examiner* — Noble E Jarrell
*Assistant Examiner* — Richard Grant Peckham
(74) *Attorney, Agent, or Firm* — HUESCHEN AND SAGE

(57) ABSTRACT

Crystalline forms of Compound A:

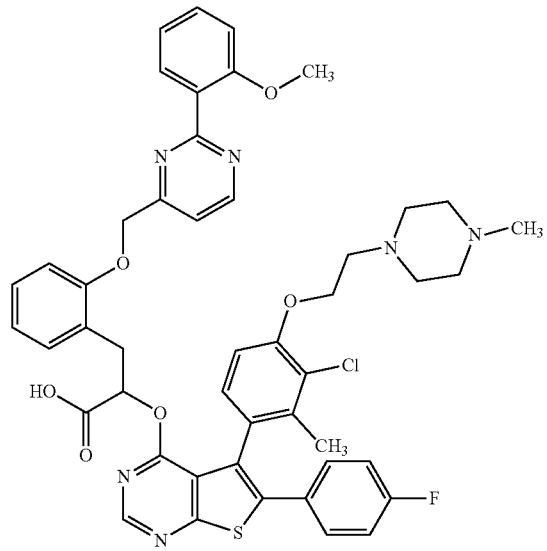

characterized by its X-ray powder diffraction diagram, solid-state $^{13}C$ NMR spectrum, MIR spectrum and Raman spectrum and pharmaceutical compositions containing it.

18 Claims, 13 Drawing Sheets

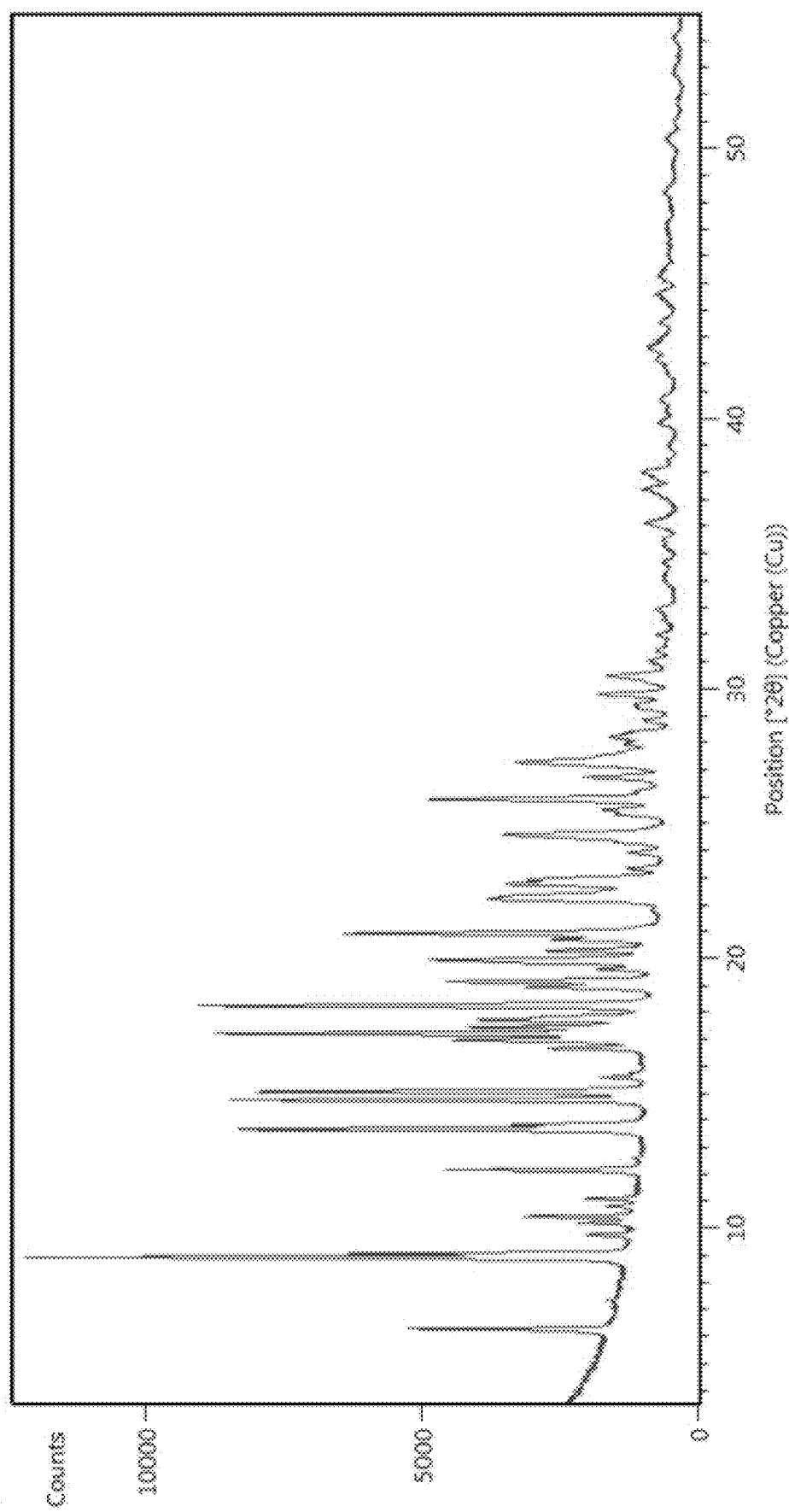
Figure 1: X-ray powder diffraction pattern (XRPD) of Compound A, crystalline Form M (3.5° to 55° 2 theta)

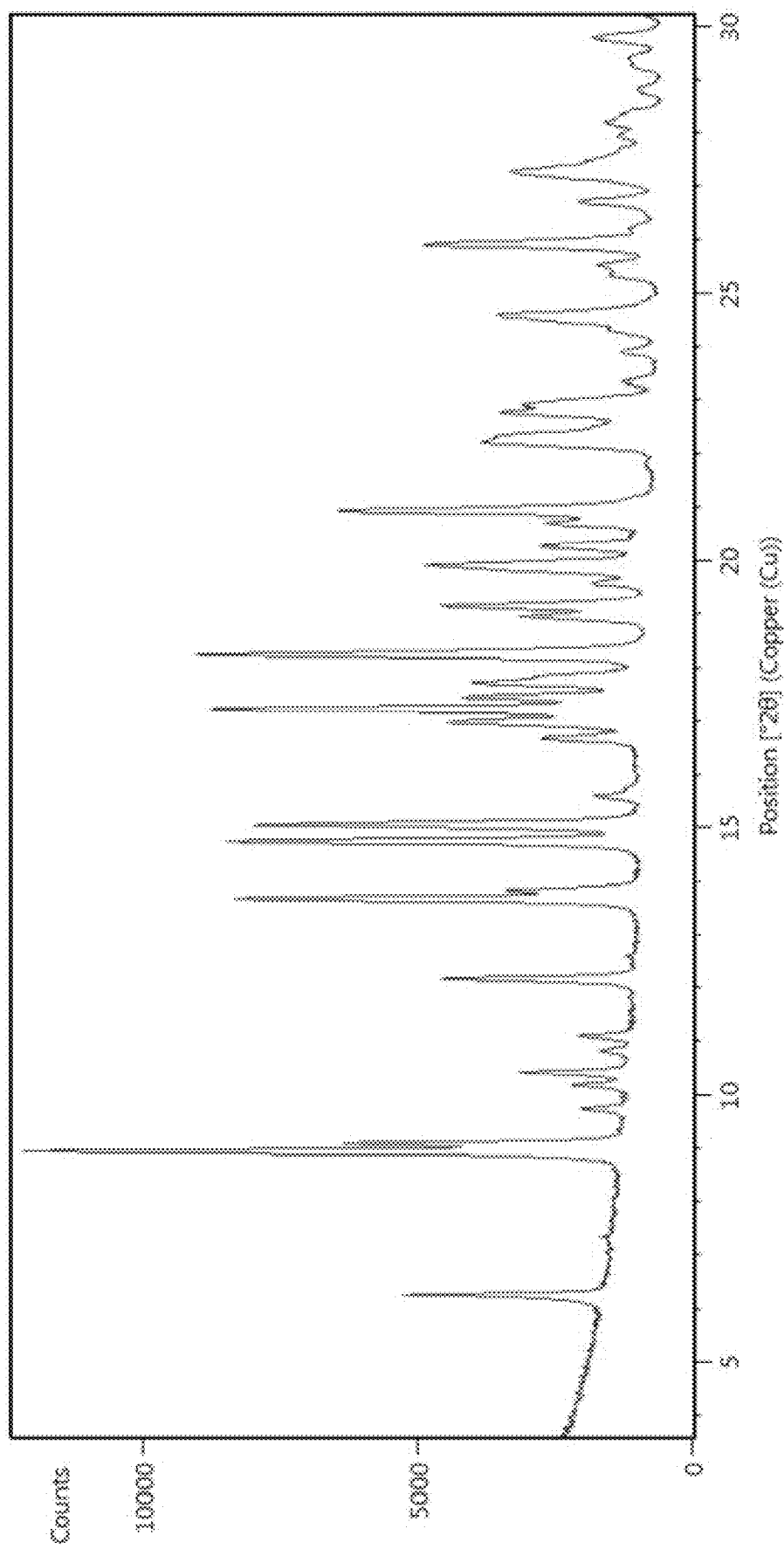
Figure 2: X-ray powder diffraction pattern (XRPD) of Compound A, crystalline Form M (3.5° to 30° 2 theta)

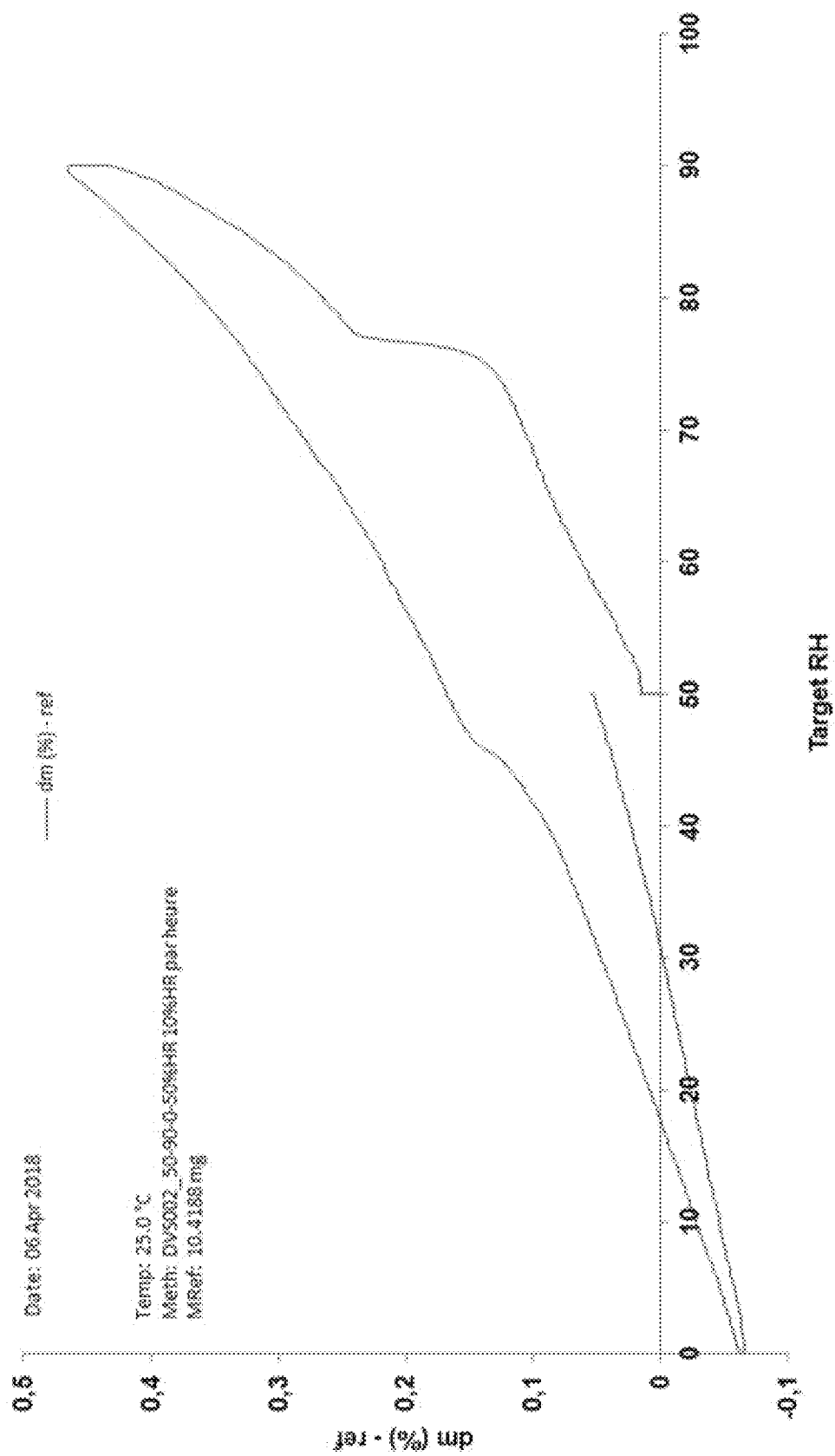

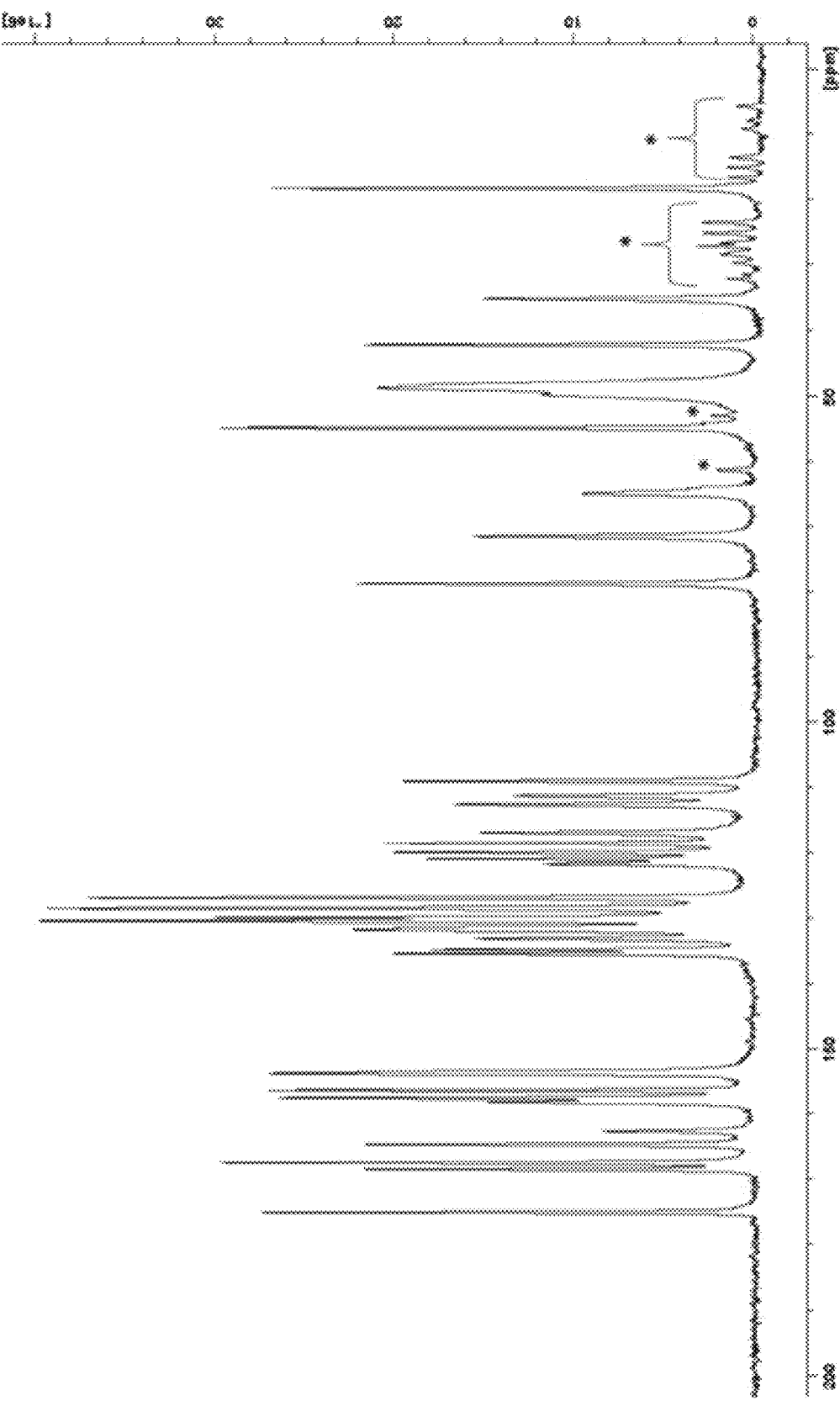

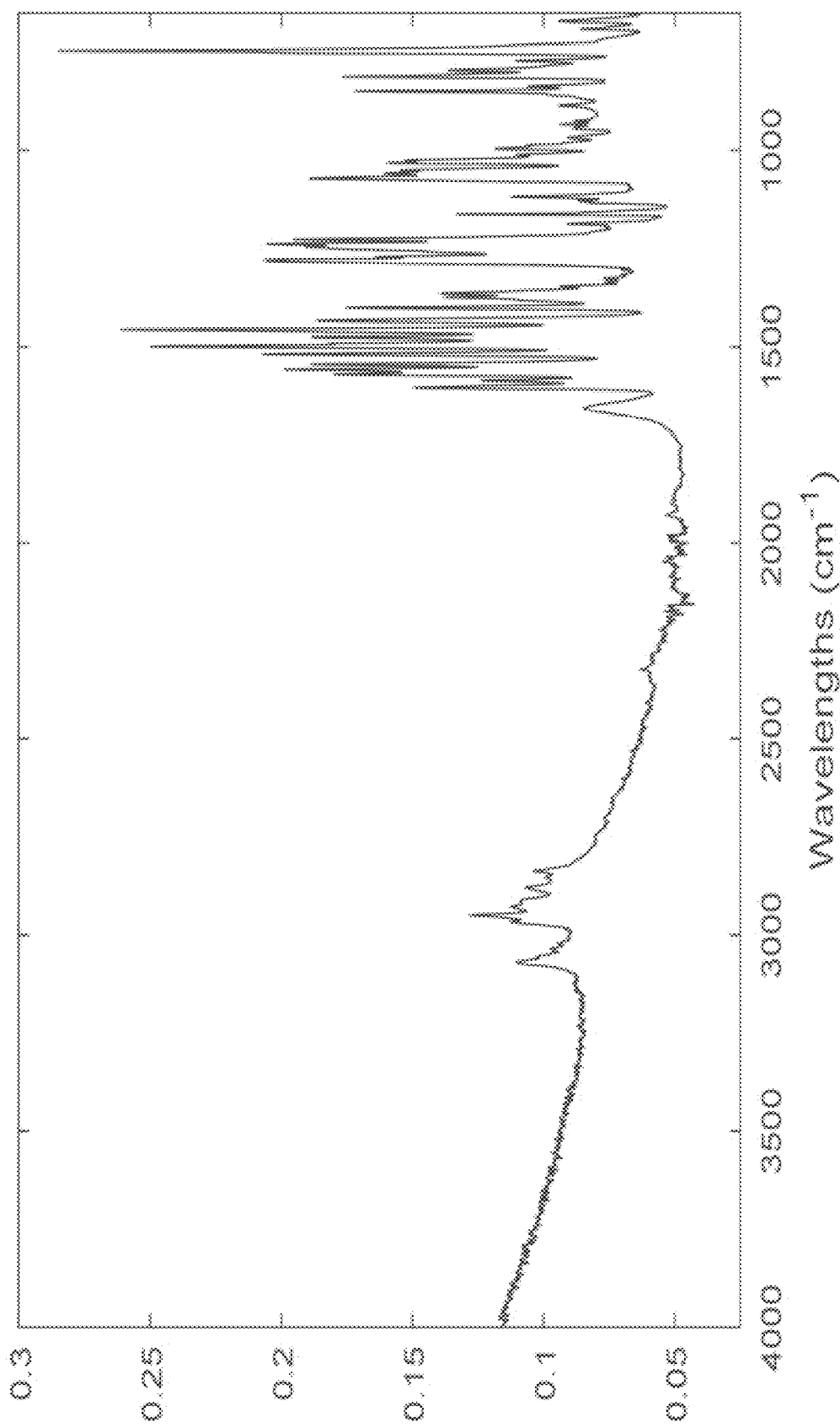

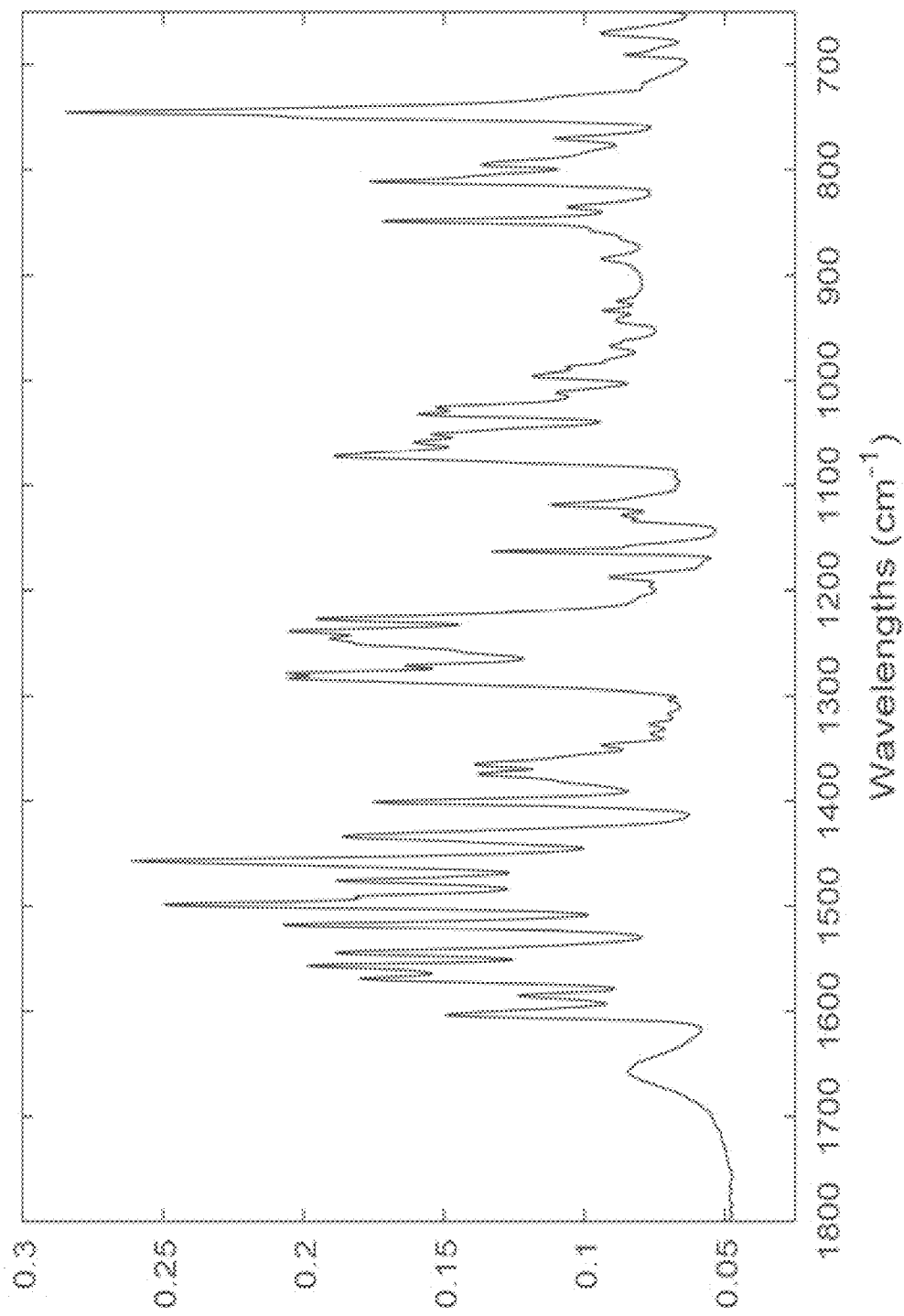
Figure 6: Mid-infra-red spectrum of Compound A, crystalline Form M (1800-650 cm⁻¹)

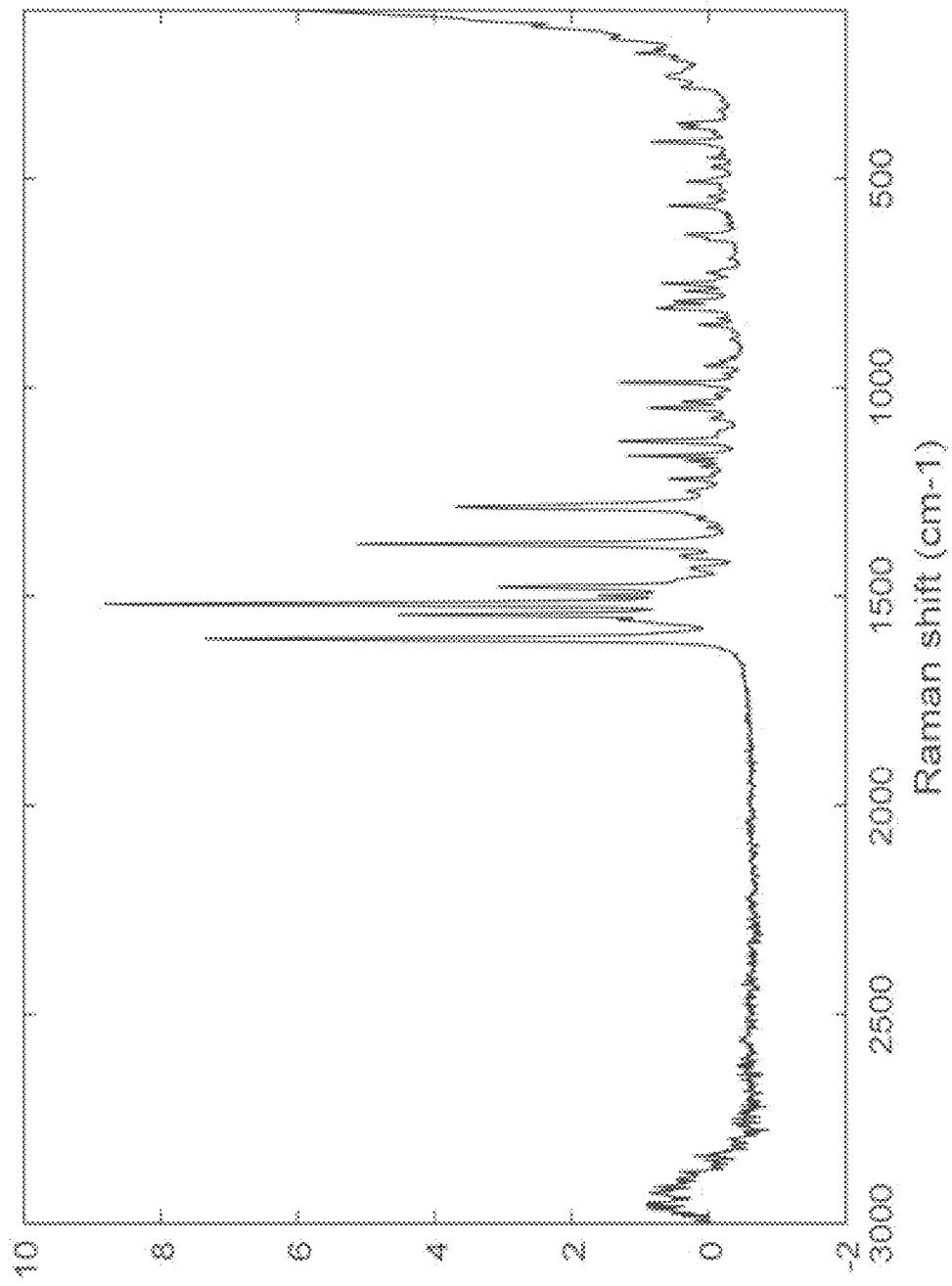

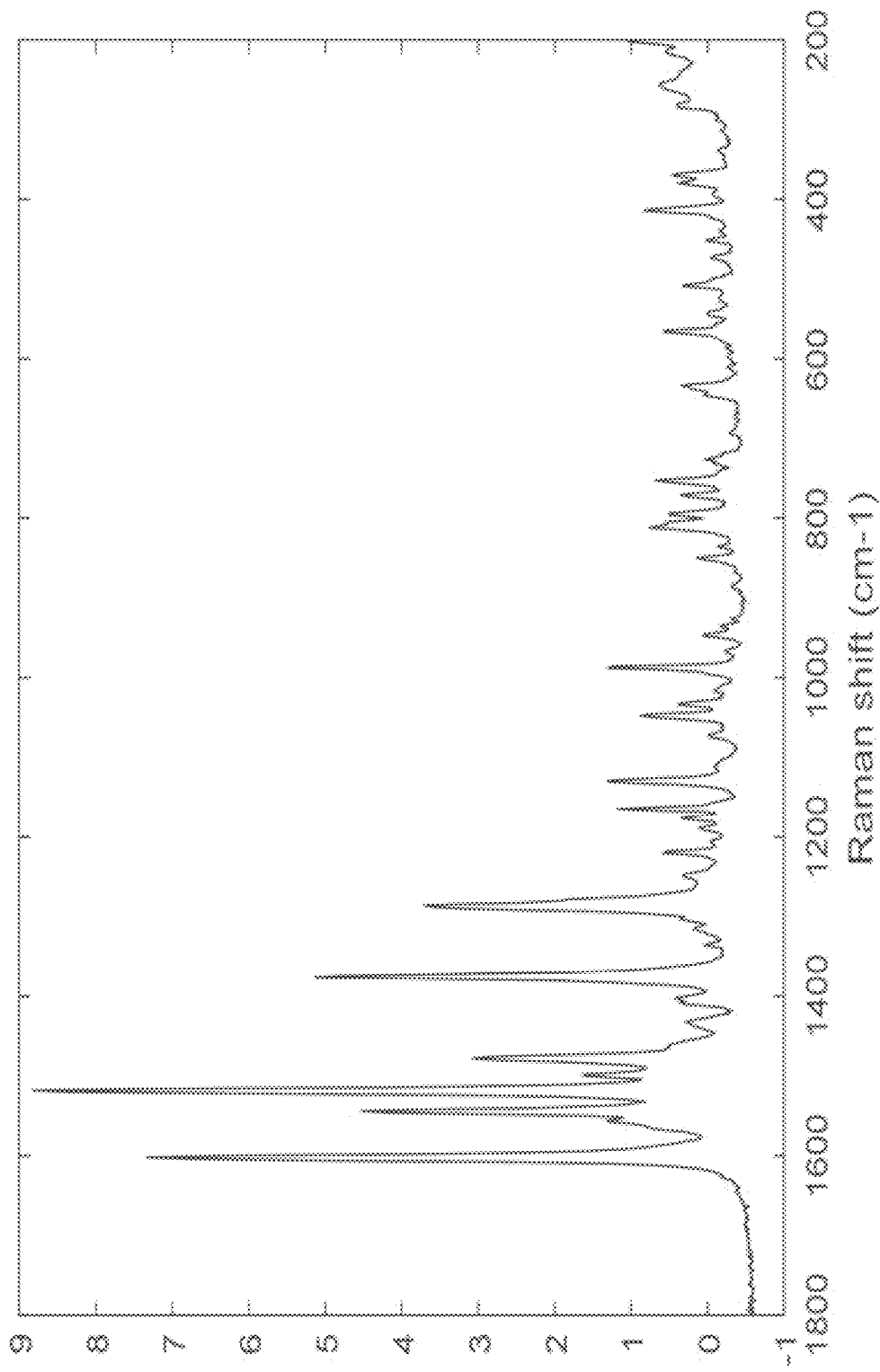
Figure 8: Raman spectrum of Compound A, crystalline Form M1 (1800-200 cm⁻¹)

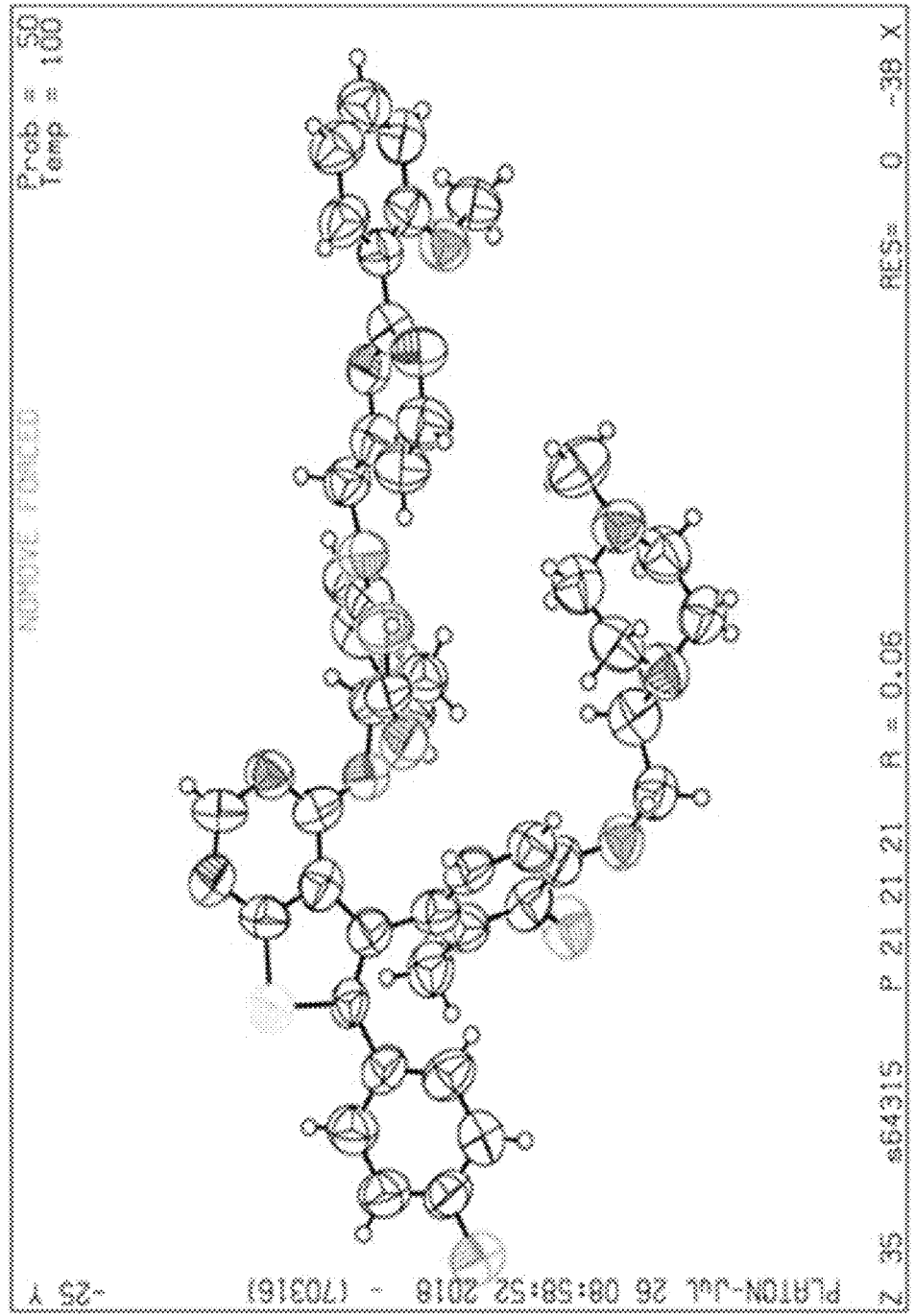
Figure 9: Thermal ellipsoid view of Compound A, crystalline Form M (Soleil Synchrotron, Saclay)

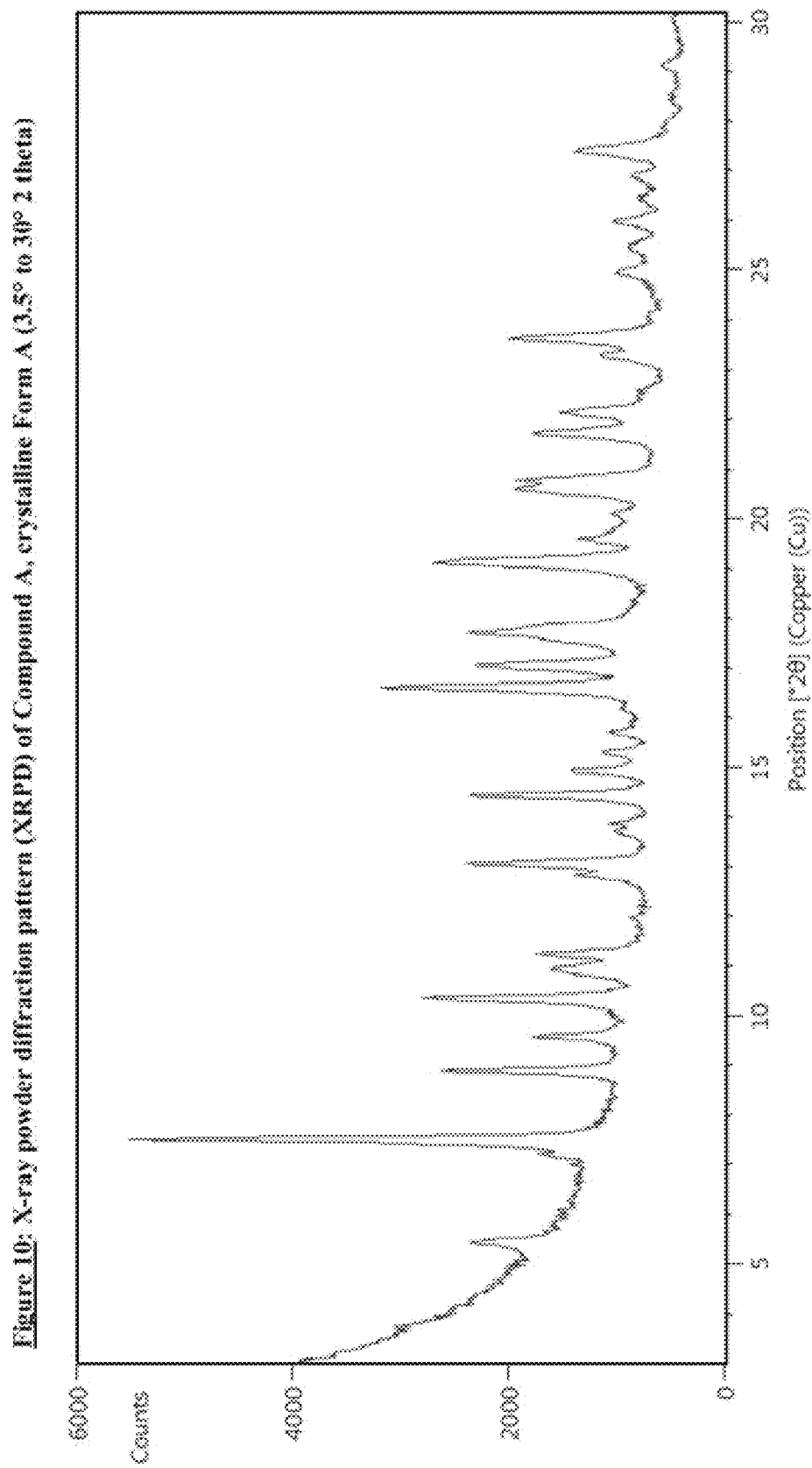

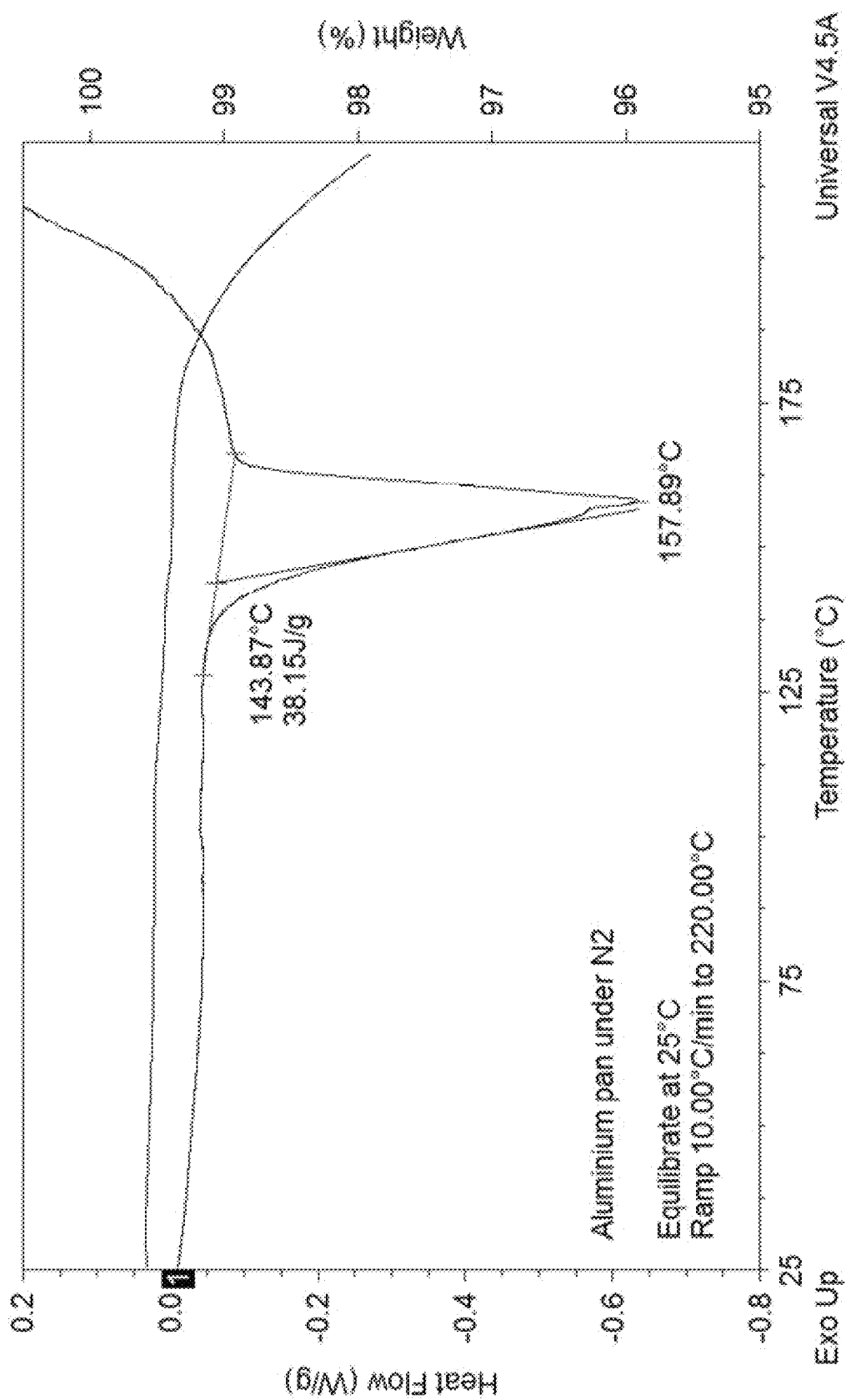
Figure 11: DSC and TGA profiles of Compound A, crystalline Form M

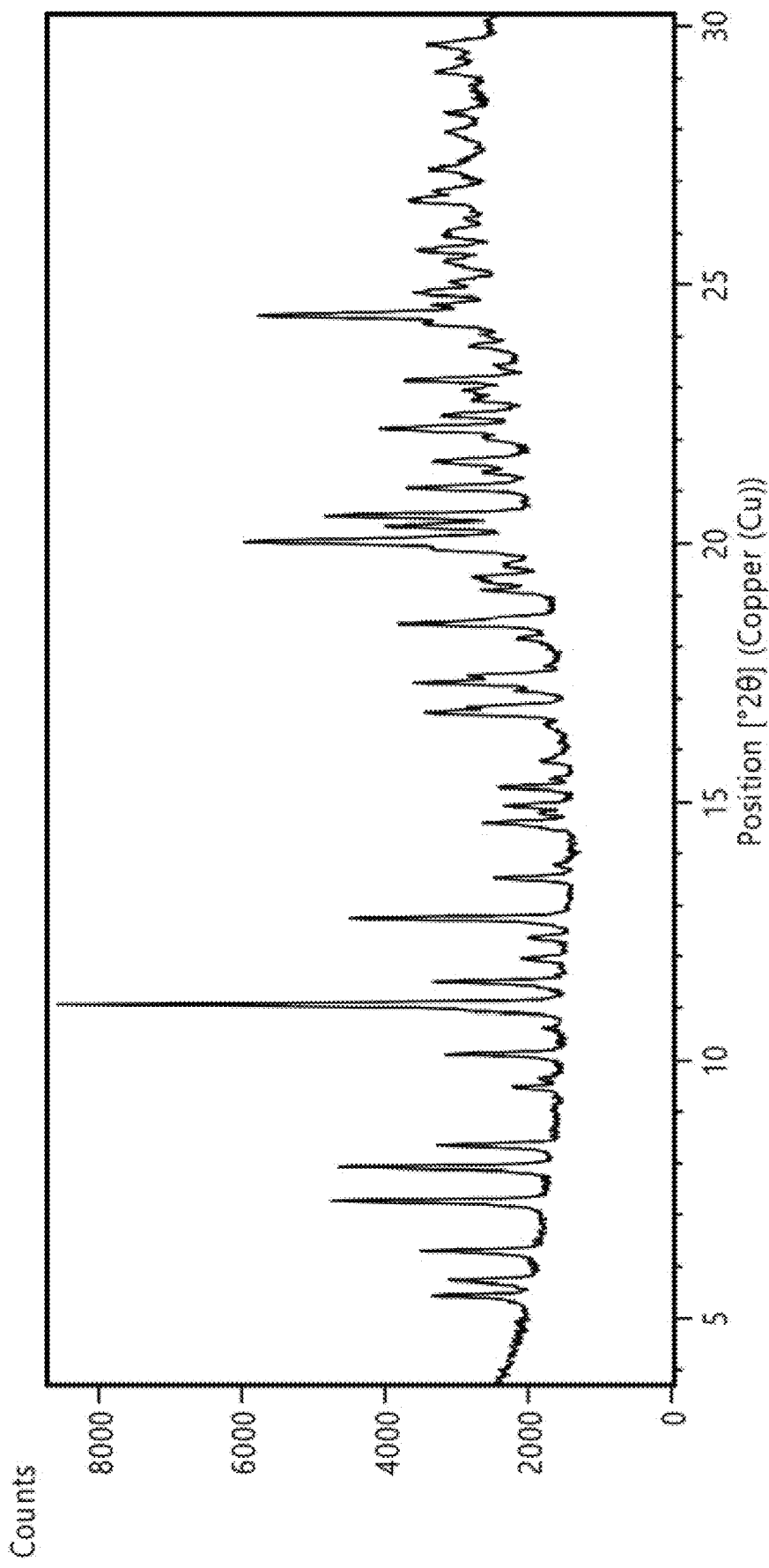
Figure 12: X-ray powder diffraction pattern (XRPD) of Compound A, crystalline Form M₁₁ (3.5° to 30° 2 theta)

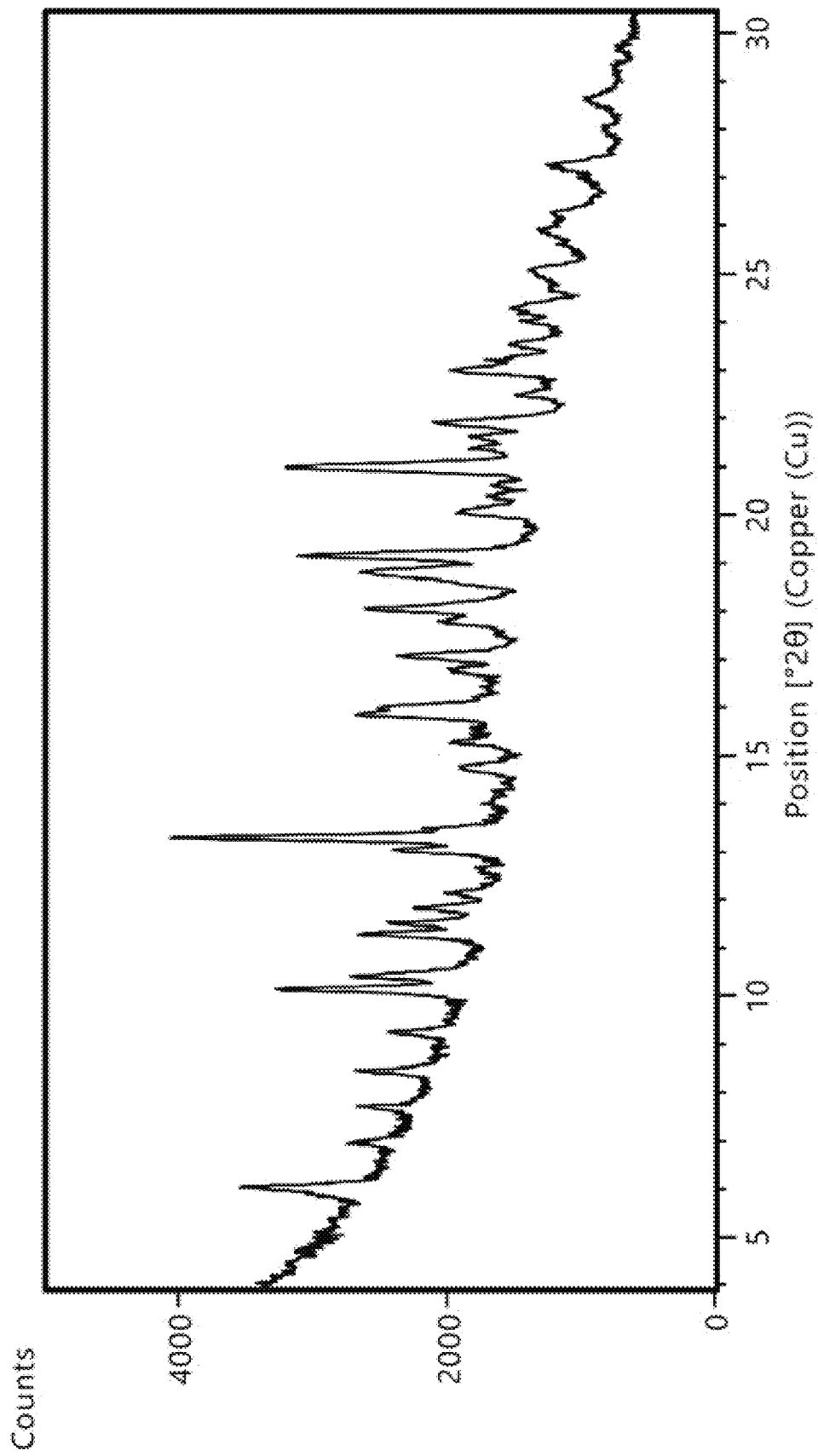
Figure 13: X-ray powder diffraction pattern (XRPD) of Compound A, crystalline Form M110 (3.5° to 30° 2 theta)

CRYSTALLINE FORMS OF A MCL-1 INHIBITOR, A PROCESS FOR THEIR PREPARATION AND PHARMACEUTICAL COMPOSITIONS CONTAINING THEM

FIELD OF THE INVENTION

The invention relates to new crystalline forms of 2-{[5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid, referred to herein as Compound A. Crystalline forms of 2-{[5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-({[2-(2-methoxyphenyl)pyrimidin-4-yl]methoxy}phenyl)propanoic acid are described herein, also referred as crystalline Forms A and M. Moreover, two other crystalline forms of 2-{[5-{3-chloro-2-methyl-4-[2-(4-methylpiperazin-1-yl)ethoxy]phenyl}-6-4-fluorophenyl)thieno[2,3-d]pyrimidin-4-yl]oxy}-3-(2-{[2-(2-methoxyphenyl)pyrimidin-4-yl]methoxy}phenyl) propanoic acid are also described herein, referred as crystalline Forms $M_H$ and $M_{HD}$.

The present invention further discloses the process for preparing said crystalline forms of 2-{[5-{3-chloro-2-methyl-4-[2-(4-methylpiperazin-1-yl)ethoxy]phenyl}-6-(4-fluorophenyl)thieno[2,3d]pyrimidin-4-yl]oxy}-3-(2-{[2-(2-methoxyphenyl)pyrimidin-4-yl]methoxy}phenyl)propanoic acid.

The present invention further discloses pharmaceutical compositions comprising said crystalline forms or 2-{[5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl) pyrimidin-4-yl]methoxy}phenyl)propanoic acid and the use of said compositions for the treatment of cancer, diseases of the immune system and auto-immune diseases.

BACKGROUND OF THE INVENTION

2-{[5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid.

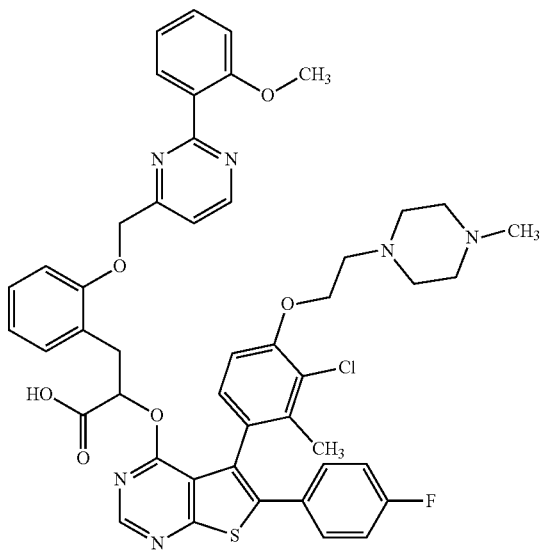 [SMILES: COc1ccccc1-c1nccc(COc2ccccc2CC(Oc2ncnc3sc(-c4ccc(F)cc4)c(-c4ccc(OCCN5CCN(C)CC5)c(Cl)c4C)c23)C(=O)O)n1]

is a Mcl-1 inhibitor useful for the treatment of cancer, diseases of the immune system and auto-immune diseases which preparation, use and pharmaceutical formulations thereof, are previously described in WO 2015/097123, the content of which is incorporated by reference. Its preparation is specifically disclosed in Example 30 of WO 2015/097123.

In a particular embodiment, Compound A is

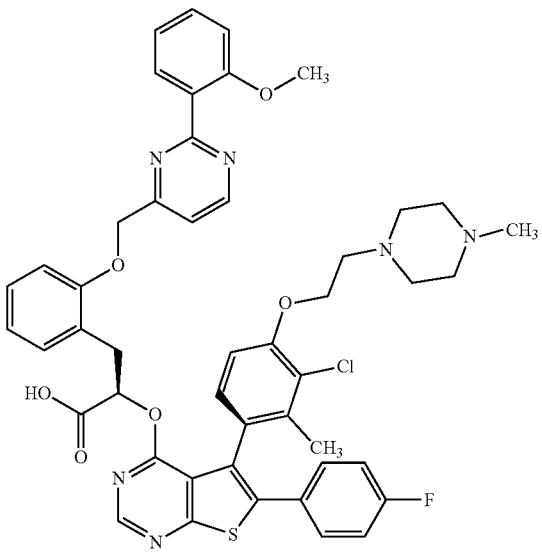

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid. In a further embodiment, Compound A used in the composition described herein is the free molecule (not a salt thereof).

Although Compound A is a very promising drug, it is a difficult compound to formulate. In water, it exhibits solubility inferior to 0.001 mg/mL (at pH 7.5). As a chemical substance can exhibit different physical properties being in one or another crystalline form, this polymorphism of the drug molecule can affect the shelf life, solubility, formulation properties, processing properties, and the action of a drug. In addition, different polymorphs can have different rates of uptake in the body, leading to lower or higher biological activity than desired. In extreme cases, an undesired polymorph can even show toxicity. Understanding and controlling polymorphism, then, gives a decided advantage in bringing new drugs to the marketplace, which may be more active, more stable, or more cheaply manufactured. However, even though polymorphism has been a subject for intensive investigations, understanding and controlling this phenomenon represents a substantial scientific challenge. It is hard to predict whether a given molecule will crystallize in one or several crystal forms, and to find conditions leading to such crystallization.

From the industrial point of view, it is imperative to be able to synthesize the compound with excellent purity, especially in a perfectly reproducible form, having valuable characteristics of dissolution, filtration, drying, ease of formulation and stability allowing its prolonged storage without particular requirements for temperature, light, humidity or oxygen levels.

The present invention relates to new crystalline forms of Compound A with the above-mentioned advantages and it also describes processes for obtaining Compound A in a well-defined, perfectly reproducible crystalline form (either Form A or Form M, particularly) having very good stability that is compatible with the industrial constraints of preparation, especially filtration, and storage of pharmaceutical compositions.

BRIEF DESCRIPTION OF THE FIGURES

FIG. 1 shows the X-ray powder diffraction pattern (XRPD) of Compound A, crystalline Form M.

FIG. 2 shows a zoom of the XRPD of Compound A, crystalline Form M.

FIG. 3 shows the water sorption profile (DVS) of Compound A, crystalline Form M.

FIG. 4 shows the solid-state $^{13}C$ NMR spectrum of Compound A, crystalline Form M.

FIG. 5 shows the mid infra-red spectrum (MIR) of Compound A, crystalline Form M.

FIG. 6 shows a zoom of the MIR spectrum of Compound A, crystalline Form M.

FIG. 7 shows the Raman spectrum of Compound A, crystalline Form M.

FIG. 8 shows a zoom of the Raman spectrum of Compound A, crystalline Form M.

FIG. 9 shows an ORTEP drawing of Compound A, crystalline Form M.

FIG. 10 shows the XRPD of Compound A, crystalline Form A.

FIG. 11 shows differential scanning calorimetry (DSC) and thermogravimetric analysis (TGA) profiles of Compound A, crystalline Form $M_H$.

FIG. 12 shows the XRPD of Compound A, crystalline Form $M_{HD}$.

FIG. 13 shows the XRPD of Compound A, crystalline Form Mud.

DETAILED DESCRIPTION OF THE INVENTION

'Compound A' means 2-{5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl) pyrimidin-4-yl]methoxy}phenyl)propanoic acid, more particularly (2R)-2-{[(5S$_a$)-5-{3-chloro-2-methyl-4-[2-(4-methylpiperazin-1-yl)elhoxy]phenyl}-6-(4-fluorophenyl)thieno [2,3-d]pyrimidin-4-yl]oxy}-3-(2-{[2-(2-methoxyphenyl)pyrimidin-4-yl]methoxy}phenyl) propanoic acid.

As used herein, the term 'comprising' means 'including', and is not intended to exclude the presence of any additional component, unless the context suggests otherwise, for example when the components together sum to 100%.

'Cancer' means a class of disease in which a group of cells display uncontrolled growth. Cancer types include hematological cancer (lymphoma and leukemia) and solid tumors including carcinoma, sarcoma, or blastoma. 'Cancer' includes bladder cancer, brain cancer, breast cancer, cancer of the uterus, chronic lymphoid leukemias, colorectal cancer, esophagus cancer, liver cancer, lymphoblastic leukemias, acute myeloid leukemia, lymphomas (for example, non-Hodgkin's B-cell lymphoma or diffuse large B-cell lymphoma), melanomas, malignant haemopathies (for example, myelodysplastic syndrome), myelomas (for example, multiple myeloma), ovarian cancer, non-small-cell lung cancer, prostate cancer, pancreatic cancer and small-cell lung cancer.

'free molecule' and 'free base' are used interchangeably herein and refer to Compound A when not in salt form.

'substantially pure', when used to crystalline form of Compound A, means having a purity greater than 90 weight %, preferably greater than 95 weight %, more preferably greater than 97 weight %, even more preferably greater than 99 weight %, and also including equal to about 100 weight % of Compound A, based on the weight of the compound.

'ICH' means International Council for Harmonization of Technical Requirements for Pharmaceuticals for Human Use.

Embodiments of the Invention

Described below are a number of embodiments of the invention.

E1. Crystalline Form M of 2-{[5-{3-chloro-2-methyl-4-[2-(4-methylpiperazin-1-yl) ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid (Compound A).

E2. Crystalline Form M of Compound A according to E1, is in substantially pure form.

E3. Crystalline Form M of Compound A according to E1 or E2, characterized in that it has an X-ray powder diffraction diagram showing at least the following diffraction lines (Bragg's angle 2 theta, expressed in degrees±0.2°); 8.94 and 18.24.

E4. Crystalline Form M of Compound A according to E1 or E2, characterized in that it has an X-ray powder diffraction diagram showing at least 4, 5, 6, 7, 8, 9, 10, 11, 12, 13, 14 or all of the following diffraction lines (Bragg's angle 2 theta, expressed in degrees±0.2°): 6.27; 8.94; 9.09; 12.16; 13.67; 14.75; 15.06; 16.97; 17.22; 17.44; 18.24; 19.16; 19.93; 20.91; 25.88.

E5. Crystalline Form M of Compound A according to E4, characterized in that it has an X-ray powder diffraction diagram having the following diffraction lines (Bragg's angle 2 theta, expressed in degrees±0.2°); 8.94; 13.67; 14.75; 17.22; 18.24.

E6. Crystalline Form M of Compound A according to E4, characterized in that it has an X-ray powder diffraction diagram having the following diffraction lines (Bragg's angle 2 theta, expressed in degrees±0.2°); 6.27; 8.94; 9.09; 12.16; 13.67; 14.75; 15.06; 16.97; 17.22; 17.44; 18.24; 19.16; 19.93; 20.91; 25.88.

E7. Crystalline Form M of Compound A according to E6, characterized in that it has the following X-ray powder diffraction diagram, measured in the spinner transmission mode using a PANalytical Empyrean diffractometer with a PIXCel ID detector and expressed in terms of line position (Bragg's angle 2 theta, expressed in degrees±0.2°) and interplanar distance d (expressed in Å):

| Line No. | Angle 2-theta (degrees) | Interplanar distance (Å) |
|---|---|---|
| 1 | 6.27 | 14.10 |
| 2 | 8.94 | 9.89 |
| 3 | 9.09 | 9.73 |
| 4 | 12.16 | 7.28 |
| 5 | 13.67 | 6.48 |

-continued

| Line No. | Angle 2-theta (degrees) | Interplanar distance (Å) |
|---|---|---|
| 6 | 14.75 | 6.00 |
| 7 | 15.06 | 5.88 |
| 8 | 16.97 | 5.22 |
| 9 | 17.22 | 5.15 |
| 10 | 17.44 | 5.08 |
| 11 | 18.24 | 4.86 |
| 12 | 19.16 | 4.63 |
| 13 | 19.93 | 4.45 |
| 14 | 20.91 | 4.25 |
| 15 | 25.88 | 3.44 |

E8. Crystalline Form M of Compound A, according to any of E1 to E7, characterized in that it has a solid-state $^{13}$C CP/MAS NMR spectrum having the following peaks (expressed in ppm±0.2 ppm): 175.1, 155.7, 134.8, 108.9, 71.4 and 35.1.

E9. Crystalline Form M of Compound A, according to any of E1 to E7, characterized in that it has a solid-state $^{13}$C CP/MAS NMR spectrum having the following peaks (expressed in ppm±0.2 ppm): 175.1, 168.5, 167.4, 164.6, 162.6, 157.5, 156.3, 153.7, 135.5, 134.8, 130.4, 129.9, 128.4, 126.8, 120.9, 119.9, 118.5, 116.9, 112.5, 111.1, 108.9, 78.7, 71.4, 54.9, 42.1, 35.1 and 18.2.

E10. Crystalline Form M of Compound A, according to any of E1 to E7, characterized in that it has a RAMAN spectrum having the following peaks (expressed in cm$^{-1}$): 1516.0, 1220.0, 770.0, 752.0, 380.0.

E11. Crystalline Form M of Compound A, according to any of E1 to E7, characterized in that it has a RAMAN spectrum having the following peaks (expressed in cm$^{-1}$): 1602.0, 1544.0, 1518.0, 1478.0, 1376.0, 1286.0, 1220.0, 1164.0, 1130.0, 1048.0, 1034.0, 988.0, 812.0, 770.0, 752.0, 634.0, 566.0, 508.0, 414.0, 380.0, 254.0.

E12. Pharmaceutical composition comprising as active ingredient crystalline Form M of Compound A, according to any one of E1 to E11 in association with one or more pharmaceutically acceptable carrier, glidant, diluent, excipient, or stabilizer.

E13. Pharmaceutical composition according to E12 for use in the treatment of cancers, auto-immune diseases and diseases of the immune system.

E14. Pharmaceutical composition for use according to E13, wherein the cancer is selected from bladder cancer, brain cancer, breast cancer, cancer of the uterus, chronic lymphoid leukemias, colorectal cancer, esophagus cancer, liver cancer, lymphoblastic leukemias, acute myeloid leukemia, lymphomas (for example, non-Hodgkin's B-cell lymphoma or diffuse large B-cell lymphoma), melanomas, malignant haemopathies (for example, myelodysplastic syndrome), myelomas (for example, multiple myeloma), ovarian cancer, non-small-cell lung cancer, prostate cancer, pancreatic cancer and small-cell lung cancer.

E15. Crystalline Form M of Compound A according to any one of E1 to E11 for use as a medicament.

E16. Crystalline Form M of Compound A according to any one of E1 to E11 for use in the treatment of cancers, auto-immune diseases and diseases of the immune system.

E17. Crystalline Form M of Compound A for use according to E16, wherein the cancer is selected from bladder cancer, brain cancer, breast cancer, cancer of the uterus, chronic lymphoid leukemias, colorectal cancer, esophagus cancer, liver cancer, lymphoblastic leukemias, acute myeloid leukemia, lymphomas (for example, non-Hodgkin's B-cell lymphoma or diffuse large B-cell lymphoma), melanomas, malignant haemopathies (for example, myelodysplastic syndrome), myelomas (for example, multiple myeloma), ovarian cancer, non-small-cell lung cancer, prostate cancer, pancreatic cancer and small-cell lung cancer.

E18. Process for the preparation of crystalline Form M of Compound A according to any one of E1 to E11, wherein Compound A is crystallized in a solvent selected from toluene, 2-methyltetrahydrofuran (Me-THF) or a mixture of toluene and methyl tert-butyl ether (MTBE), more preferably toluene or a mixture of toluene and MTBE.

E19. Process for the preparation of crystalline Form M of Compound A according to E18, wherein the solvent is a mixture of toluene and MTBE, preferably a 75/25 m/m toluene/MTBE mixture.

E20. Process for the preparation of crystalline Form M of Compound A according to E18, wherein the concentration of Compound A in the solvent is between 5 to 15% m/m, preferably between 7 to 13% m/m, more preferably between 10 to 12.5% m/m.

E21. Process for the preparation of crystalline Form M of Compound A according to any one of E18 to E20, wherein the suspension of Compound A in the solvent obtained during the process is filtered and dried under vacuum between 20° C. and 80° C., preferably between 20° C. and 75° C. more preferably between 35° C. and 75° C.

E22. Process for the preparation of crystalline Form M of Compound A according to E19, wherein the suspension of Compound A in the solvent obtained during the process is filtered and dried in two steps comprising:
a first step in which the filtrated solid is dried under vacuum at 20° C. until reaching ICH residual solvent limit for MTBE, and
a second step in which the solid obtained in the first step is dried under vacuum at 70° C. until reaching ICH residual solvent limit for toluene.

E23. Process for the preparation of crystalline Form M of Compound A according to any one of E18 to E22, in which the crystallization is seeded using a very small amount of crystalline Form M of Compound A, particularly the crystallization is seeded using 0.5% to 5% m/m of crystalline Form M of Compound A, preferably 0.5% to 3%.

E24. Process for the preparation of crystalline Form M of Compound A according to E23, wherein the crystallization is seeded at a temperature comprised between 20° C. and 60° C.

E25. Process for the preparation of crystalline Form M of Compound A according to E24, wherein the crystallization is seeded between 30° C. and 45° C.

E26. Crystalline Form A of 2-{[5-{3-Chloro-2-methyl-4-[2-(4-methylpiperazin-1-yl) ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid (Compound A).

E27. Crystalline Form A of Compound A according to E26, is in substantially pure form.

E28. Crystalline Form A of Compound A according to E26 or E27, characterized in that it has an X-ray powder diffraction diagram showing at least the following diffraction lines (Bragg's angle 2 theta, expressed in degrees±0.2°): 7.52 and 16.61.

E29. Crystalline Form A of Compound A according to E26 or E27, characterized in that it has an X-ray powder diffraction diagram showing at least 4, 5, 6, 7, 8, 9, 10, 11, 12, 13, 14, 15, 16 or all of the following diffraction lines (Bragg's angle 2 theta, expressed in degrees±0.2°): 7.52; 8.89; 9.58; 10.35; 11.25; 13.08; 14.44: 16.61: 17.07; 17.71; 19.10; 20.60; 20.80; 21.69; 22.14; 23.63; 27.36.

E30. Crystalline Form A of Compound A according to E29, characterized in that it has an X-ray powder diffraction diagram having the following diffraction lines (Bragg's angle 2 theta, expressed in degrees±0.2°): 7.52; 8.89; 10.35; 16.61; 19.10.

E31. Crystalline Form A of Compound A according to E29, characterized in that it has an X-ray powder diffraction diagram having the following diffraction lines (Bragg's angle 2 theta, expressed in degrees±0.2°); 7.52; 8.89; 9.58; 10.35; 11.25; 13.08; 14.44; 16.61; 17.07; 17.71: 19.10; 20.60; 20.80; 21.69; 22.14; 23.63; 27.36.

E32. Crystalline Form A of Compound A according to E31, characterized in that it has the following X-ray powder diffraction diagram, measured in the spinner transmission mode using a PANalytical Empyrean diffractometer with a PIXCel 1D detector and expressed in terms of line position (Bragg's angle 2 theta, expressed in degrees±0.2°) and interplanar distance d (expressed in Å):

| Line No. | Angle 2-theta (degrees) | Interplanar distance (Å) |
| --- | --- | --- |
| 1 | 7.52 | 11.76 |
| 2 | 8.89 | 9.95 |
| 3 | 9.58 | 9.23 |
| 4 | 10.35 | 8.55 |
| 5 | 11.25 | 7.87 |
| 6 | 13.08 | 6.77 |
| 7 | 14.44 | 6.13 |
| 8 | 16.61 | 5.34 |
| 9 | 17.07 | 5.19 |
| 10 | 17.71 | 5.01 |
| 11 | 19.10 | 4.64 |
| 12 | 20.60 | 4.31 |
| 13 | 20.80 | 4.27 |
| 14 | 21.69 | 4.10 |
| 15 | 22.14 | 4.02 |
| 16 | 23.63 | 3.77 |
| 17 | 27.36 | 3.25 |

E33. Pharmaceutical composition comprising as active ingredient crystalline Form A of Compound A, according to any one of E26 to E32 in association with one or more pharmaceutically acceptable carrier, glidant diluent, excipient or stabilizer.

E34. Pharmaceutical composition according to E33 for use in the treatment of cancers, auto-immune diseases and diseases of the immune system.

E35. Pharmaceutical composition for use according to E34, wherein the cancer is selected from bladder cancer, brain cancer, breast cancer, cancer of the uterus, chronic lymphoid leukemias, colorectal cancer, esophagus cancer, liver cancer, lymphoblastic leukemias, acute myeloid leukemia, lymphomas (for example, non-Hodgkin's B-cell lymphoma or diffuse large B-cell lymphoma), melanomas, malignant haemopathies (for example, myelodysplastic syndrome), myelomas (for example, multiple myeloma), ovarian cancer, non-small-cell lung cancer, prostate cancer, pancreatic cancer and small-cell lung cancer.

E36. Process for the preparation of crystalline Form A of Compound A according to any one of E26 to E32, wherein Compound A is crystallized in a solvent selected from dimethoxy-1,2-ethane (DME) or a mixture of dimethoxy-1,2-ethane and di-isopropylether (DIPE).

E37. Process for the preparation of crystalline Form M of Compound A according to E18, wherein Compound A is crystalline Form A of Compound A.

E38. Crystalline Form $M_H$ of 2-{[5-{3-Chloro-2-methyl-4-[2-(4-methylpiperazin-1-yl) ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid (Compound A).

E39. Crystalline Form $M_H$ of Compound A according to E38, is in substantially pure form.

E40. Crystalline Form $M_H$ of Compound A according to E38 or E39, characterized in that it has an X-ray powder diffraction diagram showing at least the following diffraction lines (Bragg's angle 2 theta, expressed in degrees±0.2°): 11.05 and 20.04.

E41. Crystalline Form Mu of Compound A according to E38 or E39, characterized in that it has an X-ray powder diffraction diagram showing at least 4, 5, 6, 7, 8, 9, 10, 11, 12, 13, 14, 15, 16, 17 or all of the following diffraction lines (Bragg's angle 2 theta, expressed in degrees±0.2°): 6.29, 7.26, 7.92, 8.35, 10.11, 11.05, 11.49, 12.74, 16.72, 17.36, 18.47, 20.04, 20.53, 21.07, 21.58, 22.22, 23.15, 24.41.

E42. Crystalline Form $M_H$ of Compound A according to E41, characterized in that it has an X-ray powder diffraction diagram having the following diffraction lines (Bragg's angle 2 theta, expressed in degrees±0.2°): 7.26, 7.92, 11.05, 12.74, 20.04, 20.53, 24.41.

E43 Crystalline Form $M_H$ of Compound A according to E41, characterized in that it has an X-ray powder diffraction diagram having the following diffraction lines (Bragg's angle 2 theta, expressed in degrees±0.2°): 6.29, 7.26, 7.92, 8.35, 10.11, 11.05, 11.49, 12.74, 16.72, 17.36, 18.47, 20.04, 20.53, 21.07, 21.58, 22.22, 23.15, 24.41.

E44. Crystalline Form $M_H$ of Compound A according to E43, characterized in that it has the following X-ray powder diffraction diagram, measured in the spinner transmission mode using a PANalytical Empyrean diffractometer with a PIXCel 1D detector and expressed in terms of line position (Bragg's angle 2 diets, expressed in degrees±0.2°) and interplanar distance d (expressed in Å):

| Line No. | Angle 2-theta (degrees) | Interplanar distance (Å) |
| --- | --- | --- |
| 1 | 6.29 | 14.056 |
| 2 | 7.26 | 12.181 |
| 3 | 7.92 | 11.170 |
| 4 | 8.35 | 10.594 |
| 5 | 10.11 | 8.751 |
| 6 | 11.05 | 8.008 |
| 7 | 11.49 | 7.699 |
| 8 | 12.74 | 6.949 |
| 9 | 16.72 | 5.304 |
| 10 | 17.36 | 5.109 |
| 11 | 18.47 | 4.805 |
| 12 | 20.04 | 4.431 |
| 13 | 20.53 | 4.326 |
| 14 | 21.07 | 4.216 |
| 15 | 21.58 | 4.118 |
| 16 | 22.22 | 4.001 |
| 17 | 23.15 | 3.841 |
| 18 | 24.41 | 3.647 |

E45. Pharmaceutical composition comprising as active ingredient crystalline Form $M_H$ of Compound A, according to any one of E38 to E44 in association with one or more pharmaceutically acceptable carrier, glidant, diluent, excipient or stabilizer.

E46. Pharmaceutical composition according to E45 for use in the treatment of cancers, auto-immune diseases and diseases of the immune system.

E47. Pharmaceutical composition for use according to E46, wherein the cancer is selected from bladder cancer, brain cancer, breast cancer, cancer of the uterus, chronic lymphoid leukemias, colorectal cancer, esophagus cancer, liver cancer, lymphoblastic leukemias, acute myeloid leukemia, lymphomas (for example, non-Hodgkin's B-cell lymphoma or diffuse large B-cell lymphoma), melanomas, malignant haemopathies (for example, myelodysplastic syndrome), myelomas (for example, multiple myeloma), ovarian cancer, non-small-cell lung cancer, prostate cancer, pancreatic cancer and small-cell lung cancer.

E48. Crystalline Form $M_{HD}$ of 2-{[5-{3-Chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl) propanoic acid (Compound A).

E49. Crystalline Form $M_{HD}$ of Compound A according to E48, is in substantially pure form.

E50. Crystalline Form $M_{HD}$ of Compound A according to E48 or E49, characterized in that it has an X-ray powder diffraction diagram showing at least the following diffraction lines (Bragg's angle 2 theta, expressed in degrees±0.2°): 13.30 and 21.00.

E51. Crystalline Form $M_{HD}$ of Compound A according to E48 or E49, characterized in that it has an X-ray powder diffraction diagram showing at least 4, 5, 6, 7, 8, 9, 10, 11, 12, 13, 14, 15, 16, 17 or all of the following diffraction lines (Bragg's angle 2 theta, expressed in degrees±0.2°): 6.03, 8.45, 10.14, 10.42, 11.29, 11.82, 13.30, 15.85, 17.07, 17.77, 18.05, 18.84, 19.14, 20.05, 21.00, 21.92, 22.99, 27.27.

E52. Crystalline Form $M_{HD}$ of Compound A according to E51, characterized in that it has an X-ray powder diffraction diagram having the following diffraction lines (Bragg's angle 2 theta, expressed in degrees±0.2°): 10.14, 13.30, 15.85, 18.05, 18.84, 19.14, 21.00.

E53. Crystalline Form $M_{HD}$ of Compound A according to E51, characterized in that it has an X-ray powder diffraction diagram having the following diffraction lines (Bragg's angle 2 them, expressed in degrees±0.2°): 6.03, 8.45, 10.14, 10.42, 11.29, 11.82, 13.30, 15.85, 17.07, 17.77, 18.05, 18.84, 19.14, 20.05, 21.00, 21.92, 22.99, 27.27.

E54. Crystalline Form $M_{HD}$ of Compound A according to E53, characterized in that it has the following X-ray powder diffraction diagram, measured in the spinner transmission mode using a PANalytical Empyrean diffractometer with a PIXCel ID detector and expressed in terms of line position (Bragg's angle 2 theta, expressed in degrees±0.2°) and interplanar distance d (expressed in Å):

| Line No. | Angle 2-theta (degrees) | Interplanar distance (Å) |
| --- | --- | --- |
| 1 | 6.03 | 14.647 |
| 2 | 8.45 | 10.459 |
| 3 | 10.14 | 8.720 |
| 4 | 10.42 | 8.491 |
| 5 | 11.29 | 7.835 |
| 6 | 11.82 | 7.484 |
| 7 | 13.30 | 6.656 |
| 8 | 15.85 | 5.591 |
| 9 | 17.07 | 5.194 |
| 10 | 17.77 | 4.990 |
| 11 | 18.05 | 4.915 |
| 12 | 18.84 | 4.710 |
| 13 | 19.14 | 4.636 |
| 14 | 20.05 | 4.429 |
| 15 | 21.00 | 4.231 |
| 16 | 21.92 | 4.056 |
| 17 | 22.99 | 3.868 |
| 18 | 27.27 | 3.270 |

E55. Pharmaceutical composition comprising as active ingredient crystalline Form $M_{HD}$ of Compound A, according to any one of E48 to E54 in association with one or more pharmaceutically acceptable carrier, glidant, diluent, excipient or stabilizer.

E56. Pharmaceutical composition according to E55 for use in the treatment of cancers, auto-immune diseases and diseases of the immune system.

E57. Pharmaceutical composition for use according to E56, wherein the cancer is selected from bladder cancer, brain cancer, breast cancer, cancer of the uterus, chronic lymphoid leukemias, colorectal cancer, esophagus cancer, liver cancer, lymphoblastic leukemias, acute myeloid leukemia, lymphomas (for example, non-Hodgkin's B-cell lymphoma or diffuse large B-cell lymphoma), melanomas, malignant haemopathies (for example, myelodysplastic syndrome), myelomas (for example, multiple myeloma), ovarian cancer, non-small-cell lung cancer, prostate cancer, pancreatic cancer and small-cell lung cancer.

Obtaining crystalline forms of Compound A, particularly crystalline Form M or crystalline Form A of Compound A, has the advantage of making it possible to prepare pharmaceutical formulations having a consistent and reproducible composition and having good characteristics of stability. Obtaining crystalline forms of Compound A, particularly crystalline Form $M_H$ or crystalline Form $M_{HD}$ of Compound A, has the advantage of making it possible to prepare pharmaceutical formulations having a consistent and reproducible composition and having good characteristics of stability.

A further aspect of the present invention is a pharmaceutical composition comprising the novel crystalline forms of Compound A, particularly crystalline Form M or crystalline Form A of Compound A, which may be formulated in accordance with standard pharmaceutical practice for use in a therapeutic treatment (including prophylactic treatment) of cancers, auto-immune diseases and diseases of the immune system in mammals including humans. A further aspect of the present invention is a pharmaceutical composition comprising the novel crystalline forms of Compound A, particularly crystalline Form $M_H$ or crystalline Form $M_{HD}$ of Compound A, which may be formulated in accordance with standard pharmaceutical practice for use in a therapeutic treatment (including prophylactic treatment) of cancers, auto-immune diseases and diseases of the immune system in mammals including humans.

A further aspect of the present invention is a pharmaceutical composition comprising the novel crystalline forms of Compound A, particularly crystalline Form M or crystalline Form A of Compound A, which may be formulated in accordance with standard pharmaceutical practice for use in a therapeutic combination for therapeutic treatment (including prophylactic treatment) of cancers, auto-immune diseases and diseases of the immune system in mammals including humans. A further aspect of the present invention is a pharmaceutical composition comprising the novel crystalline forms of Compound A, particularly crystalline Form $M_H$ or crystalline Form $M_{HD}$ of Compound A, which may be formulated in accordance with standard pharmaceutical practice for use in a therapeutic combination for therapeutic treatment (including prophylactic treatment) of cancers, auto-immune diseases and diseases of the immune system in mammals including humans.

A further aspect of the present invention is a pharmaceutical composition comprising crystalline forms of Compound A, particularly crystalline Form M or crystalline Form A of Compound A, in association with one or mere pharmaceutically acceptable carrier, glidant, diluent, excipient or stabilizer. Suitable carriers, diluents, glidants, excipients or stabilizers are well known to those skilled in the an and include materials such as carbohydrates, waxes, water soluble and/or swellable polymers, hydrophilic or hydrophobic materials, gelatin, oils, solvents, water and the like (Remington's Pharmaceutical Sciences (1995) 18th edition. Mack Publ. Co., Easton, PA). A further aspect of the present invention is a pharmaceutical composition comprising crystalline forms of Compound A, particularly crystalline Form $M_H$ or crystalline Form $M_{HD}$ of Compound A, in association with one or more pharmaceutically acceptable carrier, glidant, diluent, excipient or stabilizer. Suitable carriers, diluents, glidants, excipients or stabilizers are well known to those skilled in the art and include materials such as carbohydrates, waxes, water soluble and/or swellable polymers, hydrophilic or hydrophobic materials, gelatin, oils, solvents, water and the like (Remington's Pharmaceutical Sciences (1995) 18th edition. Mack Publ. Co., Easton, PA).

The pharmaceutical compositions of the invention will be dosed and administered in a fashion, i.e., amounts, concentrations, schedules, course, vehicles and route of administration, consistent with good medical practice. Factors for consideration in this context include the particular disorder being treated, the clinical condition of the individual patient, the cause of the disorder, the site of delivery of the agent, the method of administration, the scheduling of administration, and other factors known to medical practitioners.

Furthermore, the crystalline forms of Compound A thereby obtained, particularly crystalline Form M or crystalline Form A of Compound A, are sufficiently stable to allow its storage for an extended period without particular conditions for temperature, light, humidity or oxygen levels. In particular, the crystalline Form M of Compound A has been found to be very stable towards temperature and humidity after a 6-month storage period under various conditions. More particularly, crystalline Form M of Compound A remains stable after a 12-month storage period under 25° C./60% RH or 30° C./65% RH conditions.

The Examples herein below illustrate the invention but do not limit it in any way. In the crystallization process according to the invention. Compound A (free base), as starting material, can be obtained by any process. For example, Compound A can be synthesized according to WO 2015/097123.

EXAMPLE 1

Process for Obtaining Crystalline Form M of Compound A

At ambient temperature. Compound A was added in toluene to reach a 7% m/m (mass ratio) concentration. The mixture was stirred at ambient temperature for around 8 hours. The obtained suspension (slurry) was then nitrated and dried between 20° C. and 70° C. under vacuum in order to get the crystalline Form M of Compound A. The solid was characterized by the X-ray powder diffraction diagram as set out in Example 7.
Melting point: 148.7° C. (determined by DCS at 10° C./minutes under nitrogen using a TA Instruments Q1000 DSC)

Alternatively, the slurry obtained before filtration can be directly used as a seeding in the crystallization process as shown in Examples 2 to 5 hereinbelow.

EXAMPLE 2

Process for Obtaining Crystalline Form M of Compound A (Seeding)

Compound A (9 g: free base) was added in toluene at ambient temperature at a concentration of 6.5 mL/g or 15% m/m. The mixture was then heated to 70° C. for solubilizing Compound A. The mixture was cooled and, when temperature reached around 30° C. the solution was seeded with undried slurry of Compound A obtained in Example 1 (4.4% in weight of starting material). The mixture was further stirred for 25 hours at 5° C. The suspension was then filtered, washed with water and dried at 70° C. under vacuum. After drying, crystalline Form M of Compound A was obtained in a yield of about 87% and with purity of 99.37%. The solid was characterized by the X-ray powder diffraction diagram as set out in Example 7.

EXAMPLE 3

Alternative Process for Obtaining Crystalline Form M of Compound A

Compound A (10 g; free base) was placed in toluene at ambient temperature at a concentration of 10.4 mL/g or 10% m/m. The mixture was then heated at 70° C. and concentrated under vacuum at 60° C. to reach a concentration of 6.5 mL/g or 15% m/m. The mixture was cooled to 43° C. and was seeded with undried slurry of Compound A obtained in Example 1 (4% in weight of starting material). MTBE was added in order to obtain a 75/25 m/m toluene/MTBE solution. The final concentration of Compound A was 12% m/m. The mixture was cooled and stirred for 15 hours at 20° C. The suspension was then filtered, washed with MTBE and dried at 70° C. under vacuum. After drying, crystalline Form M of Compound A was obtained in a yield of about 89% and with purity of 99.6%. The solid was characterized by the X-ray powder diffraction diagram as set out in Example 7.

EXAMPLE 4

Alternative Process for Obtaining Crystalline Form M of Compound A

Compound A (275 g; free base) was placed in a binary toluene/acetone with a mass ratio at 75/25 toluene/acetone at ambient temperature at a concentration of 16.5% m/m. Acetone was removed from toluene by distillation under vacuum at around 50° C. After adding toluene to reach a concentration of 16.5% m/m, the mixture was healed to 40° C. and then was seeded with undried slurry of Compound A obtained in Example 1 (1% to 2% in weight of starting material). After stirring at 40° C. MTBE was slowly added in order to obtain a 75/25 m/m toluene/MTBE solution. The final concentration of Compound A was 12% m/m. The mixture was stirred for 30 minutes at 40° C. and cooled at 20° C. for 2 hours. The suspension was then filtered, washed with a 75/25 m/m toluene/MTBE solution and dried firstly at 20° C. under vacuum until reaching ICH residual solvent limit for MTBE, then dried secondly at 70° C. under vacuum until reaching ICH residual solvent limit for toluene. After drying, crystalline Form M of Compound A was obtained in a yield of about 93% and with purity greater than 99%. The solid was characterized by the X-ray powder diffraction diagram as set out in Example 7.

EXAMPLE 5

Alternative Process for Obtaining Crystalline Form M of Compound A

Compound A (free base) was placed at ambient temperature in binary mixture of 2-methyltetrahydrofuran (Me-THF)/water with around 10% of water m/m ratio at a concentration around 12% m/m. The mixture was heated at 40° C. under vacuum to replace water (by solvent switch) with Me-THF. Me-THF was added until reaching less than 1% of water in the condensate and until reaching c final volume of the mixture at 12% m/m ratio. At 40° C., the mixture was seeded (1% in weight of starting material) with a slurry of Compound A (obtained in Example 1) in Me-THF at a concentration around 7% m/m. After stirring for 1 hour, the suspension was cooled to 10° C. and it was stirred for 2 additional hours. The suspension was then filtered, washed with Me-THF and dried at 40° C. under vacuum. After drying, crystalline Form M of Compound A was obtained in a yield of about 62% and with a purity of 99.6%. The solid was characterized by the X-ray powder diffraction diagram as set out in Example 7.

EXAMPLE 6

Alternative Process for Obtaining Crystalline Form M of Compound A

Compound A (1 kg), toluene (4.2 kg) and acetone (1.4 kg) were introduced into a reactor at 20° C. for solubilization. The acetone was replaced by toluene by distillation under vacuum (temperature around 50° C.) at constant volume until reaching toluene density in condensate trap. When the toluene density was reached, the volume was adjusted with toluene to reach 16.5% of mass product rate and the temperature was kept at 50° C. After cooling at 40° C., the crystallization was induced by seeding with a suspension of Compound A in toluene (slurry at 7% mass product rate, prepared according to the process of Example 1). After 2 hours of holding time at 40° C., MTBE (1.8 kg) was added at 40° C. in one hour minimum and then the reaction was cooled to reach 20° C. Once the reaction finished, the suspension was then filtered, washed with MTBE (3.8 kg), flushed with nitrogen until reaching 10% residual solvent and dried firstly at 20° C. under vacuum until reaching ICH residual solvent limit for MTBE, then dried secondly at 70° C. under vacuum until reaching ICH residual solvent limit for toluene. After drying, crystalline Form M of Compound A was obtained in a yield of about 93% and with purity of about 99.8%. The solid was characterized by the X-ray powder diffraction diagram as set out in Example 7.

EXAMPLE 7

XRPD Diagram of Crystalline Form M of Compound A

Recording of the data in the spinner transmission mode was carried out using a PANalytical Empyrean diffractometer with a PIXCel ID detector under the following conditions:
Voltage: 45 kV
Current: 40 mA
Mounting: theta/theta
Anode: copper
K alpha-1 wave length: 1.54060 Å
K alpha-2 wavelength: 1.54443 Å
K alpha-2/K alpha-1 ratio: 0.5

Measurement mode: continuous from 3.5° to 55° (Bragg's angle 2 theta) in Increments of 0.017°
Measurement time per step: 34.9250 s The X-ray powder diffraction diagram or Form M of Compound A obtained according to any one of the processes of Examples 1 to 6 is expressed in terms of line position (Bragg's angle 2 theta, expressed in degrees±0.2°) and interplanar distance (expressed in Å) (FIGS. 1 and 2). The significant lines have been collated in the following table:

| Line No. | Angle 2-theta (degrees) | Interplanar distance (Å) |
|---|---|---|
| 1 | 6.27 | 14.10 |
| 2 | 8.94 | 9.89 |
| 3 | 9.09 | 9.73 |
| 4 | 12.16 | 7.28 |
| 5 | 13.67 | 6.48 |
| 6 | 14.75 | 6.00 |
| 7 | 15.06 | 5.88 |
| 8 | 16.97 | 5.22 |
| 9 | 17.22 | 5.15 |
| 10 | 17.44 | 5.08 |
| 11 | 18.24 | 4.86 |
| 12 | 19.16 | 4.63 |
| 13 | 19.93 | 4.45 |
| 14 | 20.91 | 4.25 |
| 15 | 25.88 | 3.44 |

EXAMPLE 8

Hygroscopicity

The hygroscopicity of crystalline Form M of Compound A obtained according to any one of the processes of Examples 1 to 6 was assessed using the dynamic vapor sorption (DVS) technique. 5 to 10 mg of the drug substance test sample were accurately weighed into a DVS sample pan working at 25° C. under controlled humidity. The mass of the sample was recorded at 50% RH (relative humidity) until reaching a stable value. Thereafter the mass variation was recorded between 50% RH and 90% RH at a rate of 10% per hour. Mass variations were also recorded between 90% RH and 0% RH and from 0% RH back to 50% RH. The relative humidity was maintained constant when it reached either 0 or 90% RH until the mass variation was less than 0.002% per minute within a limit of lime of 15 hours. An increase in sample mass of approximately 0.4% was recorded by DVS analysis when a sample was exposed to relative humidities from 50% to 90% at 25° C.

A decrease in sample moss was of approximately 0.5% was recorded between 90% to 0% RH, whilst an increase in sample mass of approximately 0.1% was recorded between 0% to 50% RH.

The DVS profile (FIG. 3) shows that water sorption and desorption are practically reversible with no change to the crystalline from M observed in the X-ray powder diffractogram after the water sorption/desorption/sorption cycle.

Crystalline Form M of Compound A can be considered as being slightly hygroscopic according to the European Pharmacopoeia (Ph. Eur.).

EXAMPLE 9

Coulometric Titration

The water content of crystalline Form M of Compound A obtained according to any one of the processes of Examples 1 to 6 was determined by coulometric titration using a Metrohm Coulometer composed of a 774 oven sample processor, a 774 SC controller, 831 KF coulometer and a 846

Dosing interface with Tiamo 1.2 software About 10 mg of accurately weighed micronized drug substance were introduced in vials heated for 10 minutes at 140° C.

The water content in the test samples amounted to 0.1% in weight.

EXAMPLE 10

Stability Studies of Crystalline Form M of Compound A

For all storage conditions and storage periods, 20 mg of crystalline Form M of Compound A obtained according to any one of the processes of Examples 1 to 6 were introduced in a 30-mL vial for post-storage HPLC analysis (packaging: PVO=Opened glass container; VRAC PA=Double polyethylene bag). Results areas follows:

| Storage periods | 25° C. 60% RH VRAC PA | 25° C. 90% RH PVO | 30° C. 65% RH VRAC PA | 40° C. 75% RH VRAC PA | 50° C. 75% RH PVO |
|---|---|---|---|---|---|
| | Storage conditions | | | | |
| | (i) Polymorphic and (ii) chemical stabilities (% m/m)* | | | | |
| 6 weeks | | | | | (i) Form M (ii) 100.2% |
| | | | | | |
| | | | | | (ii) 100.0% |
| 3 months | (i) not tested (ii) 100.0% | (i) Form M (ii) 99.7% | (i) not tested (ii) 99.6% | (i) Form M (ii) 99.9% | (i) Form M (ii) 100.1% |
| 6 months | (i) not tested (ii) 99.7% | | (i) not tested (ii) 100.0% | (i) Form M (ii) 100.0% | |
| 12 months | (i) Form M (ii) 98.9% | | (i) Form M (ii) 98.8% | | |

*drug substance content determined by LC (% m/m)

Crystalline Form M of Compound A remains stable towards temperature and humidity after a 6-month storage period under various conditions. More particularly, crystalline Form M of Compound A remains stable after a 12-month storage period under 25° C./60% RH or 30° C./65% RH conditions.

EXAMPLE 11

Solid-State $^{13}$C NMR Spectrum of Crystalline Form M of Compound A

Crystalline Form M of Compound A obtained according to any one of the processes of Examples 1 to 6 was also characterized by solid-state $^{13}$C Nuclear Magnetic Resonance spectroscopy (FIG. 4). The solid-state $^{13}$C NMR spectrum of Compound A crystalline Form M was recorded at ambient temperature using a Bruker SB Avance III 500 spectrometer with a 4-mm CP/MAS SB VTN type probe under the following conditions:

Frequency: 125.7 MHz
Spectral width: 37.5 kHz
Magic angle spinning rate: 13 kHz
Pulse program: Cross Polarization with SPINAL64 decoupling
Recycle delay: 10 seconds
Acquisition time: 46 milliseconds
Contact time: 4 milliseconds
Number of scans: 2048

A 5 Hz line-broadening was applied prior to Fournier Transform. The spectrum thereby obtained was referenced relative to a sample of adamantane (the high frequency peak of adamantane is set to 38.5 ppm). Compound A, crystalline Form M can be defined by the presence of the following peaks in the NMR spectrum (expressed in ppm±0.2 ppm):

| Peak no. | Chemical shift (ppm) | Δδ ppm (−18.2 ppm) | Peak no. | Chemical shift (ppm) | Δδ ppm (−18.2 ppm) |
|---|---|---|---|---|---|
| 1 | 175.1 | 156.9 | 15 | 120.9 | 102.7 |
| 2 | 168.5 | 150.3 | 16 | 119.9 | 101.7 |
| 3 | 167.4 | 149.2 | 17 | 118.5 | 100.3 |
| 4 | 164.6 | 146.4 | 18 | 116.9 | 98.7 |
| 5 | 162.6 | 144.4 | 19 | 112.5 | 94.3 |
| 6 | 157.5 | 139.3 | 20 | 111.1 | 92.9 |
| 7 | 156.3 | 138.1 | 21 | 108.9 | 90.7 |
| 8 | 153.7 | 135.5 | 22 | 78.7 | 60.5 |
| 9 | 135.5 | 117.3 | 23 | 71.4 | 53.2 |
| 10 | 134.8 | 116.6 | 24 | 54.9 | 36.7 |

-continued

| Peak no. | Chemical shift (ppm) | Δδ ppm (−18.2 ppm) | Peak no. | Chemical shift (ppm) | Δδ ppm (−18.2 ppm) |
|---|---|---|---|---|---|
| 11 | 130.4 | 112.2 | 25 | 42.1 | 23.9 |
| 12 | 129.9 | 111.7 | 26 | 35.1 | 16.9 |
| 13 | 128.4 | 110.2 | 27 | 18.2 | 0 |
| 14 | 126.8 | 108.6 | | | |

The column entitled "Δδ ppm" indicates the relative chemical shifts, in ppm, of all peaks relative to the lowest peak in ppm identified in the $^{13}$C spectrum of Form M.

More particularly, characteristic peaks are at (expressed in ppm±0.2 ppm): 175.1, 153.7, 134.8, 108.9, 71.4 and 35.1.

EXAMPLE 12

MIR Spectrum of Crystalline Form M of Compound A

Crystalline Form M of Compound A obtained according to any one of the processes of Examples 1 to 6 was also characterized by Mid-Infra-Red spectroscopic method which data were recorded in the ATR mode using a Bruker Vertex MIR spectrometer under the following conditions:

Number of scans: 32
Resolution: 2 cm$^{-1}$

The MIR spectrum of crystalline Form M of Compound A is given in FIGS. 5 and 6. Characteristic peaks are at (expressed in cm$^{-1}$): 1603.7, 1569.0, 1556.5, 1544.9 1517.9, 1498.6, 1475.5, 1457.1, 1434.0, 1401.2, 1374.2, 1364.6, 1278.7, 1239.2, 1226.7, 1187.1, 1163.0, 1118.7, 1072.4, 1031.9, 995.2, 884.3, 848.6, 811.0, 795.6, 770.5, 745.5, 690.5, 670.2.

More particularly, characteristic peaks are at (expressed in cm$^{-1}$): 1475.5, 1457.1, 1434.0, 1278.7, 1226.7, 848.6, 770.5, 745.5.

EXAMPLE 13

RAMAN Spectrum of Crystalline Form M of Compound A

Crystalline Form M of Compound A obtained according to any one of the processes of Examples 1 to 6 was also characterized by Raman spectroscopic method which data were recorded using a Perkin-Elmer RS400 Raman spectrometer under the following conditions:
Number of scans: 10
Imposition lime: 0.5 seconds
Laser power: 100%

The Raman spectrum of crystalline Form M of Compound A is given in FIGS. 7 and 8. Characteristic peaks are at (expressed in cm$^{-1}$): 1602.0, 1544.0, 1518.0, 1478.0, 1376.0, 1286.0, 1220.0, 1164.0, 1130.0, 1048.0, 1034.0, 988.0, 812.0, 770.0, 752.0, 634.0, 566.0, 508.0, 414.0, 380.0, 254.0.

More particularly, characteristic peaks are at (expressed in cm$^{-1}$): 1516.0, 1220.0, 770.0, 752.0, 380.0.

EXAMPLE 14

Purify of Crystalline Form M of Compound A Determined by Synchrotron Radiation (Sotei Synchrotron, Saclay, France)

A suitable crystal of crystalline Form M of Compound A was selected and mounted onto the synchrotron beamline PROXIMA II diffractometer (SOLEIL, Saclay, France). The crystal was kept at 100 K during data collection. Using Olex2 (Dolomanov et al., *J. Appl. Cryst.* 2009, 42, 339-3411), the structure was solved with the ShelXT structure solution program using Intrinsic Phasing (Sheldrick, *Acta Cryst.* 2015, A71, 3-8) and refined with the ShelXL refinement package using Least Squares Minimisation (Sheldrick, *Acta Cryst.* 2015, C71, 3-8). Positions and atomic displacement parameters were refined by full-matrix least-squares routines against F$^2$. Hydrogen atoms were placed using riding model. Absolute structure has been determined and is in line with the pure enantiomeric phase of Compound A.

1. Synchrotron data recorded at 100 K, together with the thermal ellipsoid view of the asymmetric unit (I molecule of Compound A):
Space group P212121 (No. 19)
a=10.610 Å
b=17.400 Å
c=23.720 Å
V=4379.0 Å$^3$
Z=4
T=100 K FIG. 9 shows the thermal ellipsoid view (obtained by using ORTEP program) of Compound A, crystalline Form M.

2. Crystal lattice parameters obtained from the X-ray powder diffractogram of Compound A Form M) at room temperature:
Space group P2$_1$2$_1$2$_1$ (No. 19)
a=10.6401 Å
b=17.3643 Å
c=24.0494 Å
V=4443.3 Å$^3$
Z=4
T=293 K 3. Peak positions and interplanar distances (d$_{hkl}$) calculated from data obtained from the monocrystal (at 100 K)

| List of selected peaks with peak intensities 25 times that of the noise level intensity (I/σI ≥ 25) 100 K | |
|---|---|
| 2 theta (°) | Interplanar distance (Å) |
| 6.29 | 14.03 |
| 9.02 | 9.80 |
| 9.12 | 9.68 |
| 12.29 | 7.20 |
| 13.67 | 6.47 |
| 14.86 | 5.96 |
| 15.13 | 5.85 |
| 17.12 | 5.18 |
| 17.29 | 5.12 |
| 18.30 | 4.84 |
| 19.38 | 4.58 |
| 19.94 | 4.45 |
| 21.12 | 4.20 |
| 22.47 | 3.95 |
| 24.71 | 3.60 |
| 26.12 | 3.41 |

The set of peaks obtained from single crystal data matches closely those measured experimentally (see Example 7 for comparison). Consequently, these results confirm the high purity of Compound A, crystalline Form M.

EXAMPLE 15

Process for Obtaining Crystalline Form A of Compound A and X-ray Powder Diffraction Diagram of the Same Compound A was dissolved in 2-methyltetrahydrofuran at ambient temperature at a concentration of 8 mL/g and dimethoxy-1,2-ethane (DME) was added to reach a concentration of 11 mL/g. Then the mixture was stirred at 35° C. for 2 hours and 3 hours at 20° C. After crystallization, the solid was filtered, washed with acetone and dried under vacuum at 50° C. then at 70° C. After drying, crystalline Form A of Compound A was obtained in a yield of about 81% and with purity of 99.5%. The solid was characterized by the X-ray powder diffraction diagram as described below.
Melting point: 125.4° C. (determined by DSC at 10° C./minutes under nitrogen using a TA Instruments Q1000 DSC)

A variant of the process for obtaining Form A of Compound A (seeding) is as follows:

Compound A was dissolved in 2-methyltetrahydrofuran at ambient temperature at a concentration of about 11 mL/g and DME was added to reach a concentration of 11 mL/g. A quarter of solvent was removed by distillation and DME was added again to reach a concentration of 11 mL/g. Then the mixture was heated at 35° C. and was seeded with Form A of Compound A (2% in weight of starting material). The mixture was stirred at 35° C. for 2 hours and 19 hours at 20° C. After crystallization, the solid was filtered, washed with acetone and dried under vacuum at 50° C. then at 70° C. After drying, crystalline Form A of Compound A was obtained in a yield of about 93% and with purity greater than 99.0%. The solid was characterized by the X-ray powder diffraction diagram as described below.

Recording of the data in the spinner transmission mode was carried out using a PANalytical Empyrean diffractometer with a PIXCel ID detector under the following conditions:
Voltage: 45 kV
Current: 40 mA
Mounting: theta/theta Anode: copper
K alpha-1 wavelength: 1.54060 Å
K alpha-2 wavelength: 1.54443 Å
K alpha-2/K alpha-1 ratio: 0.5
Measurement mode: continuous from 3.5° to 55° (Bragg's angle 2 theta) in increments of 0.017°
Measurement time per step: 34.9250 s The X-ray powder diffraction diagram of Form A of Compound A is expressed in terms of line position (Bragg's angle 2 theta, expressed in degrees±0.2°) and interplanar distance (expressed in Å) (FIG. 10). The significant lines have been collated in the following table:

| Line No. | Angle 2-theta (degrees) | Interplanar distance (Å) |
|---|---|---|
| 1 | 7.52 | 11.76 |
| 2 | 8.89 | 9.95 |
| 3 | 9.58 | 9.23 |
| 4 | 10.35 | 8.55 |
| 5 | 11.25 | 7.87 |
| 6 | 13.08 | 6.77 |
| 7 | 14.44 | 6.13 |
| 8 | 16.61 | 5.34 |
| 9 | 17.07 | 5.19 |
| 10 | 17.71 | 5.01 |
| 11 | 19.10 | 4.64 |
| 12 | 20.60 | 4.31 |
| 13 | 20.80 | 4.27 |
| 14 | 21.69 | 4.10 |
| 15 | 22.14 | 4.02 |
| 16 | 23.63 | 3.77 |
| 17 | 27.36 | 3.25 |

EXAMPLE 16

Process for Obtaining Crystalline Form M gf Compound A from Crystalline Form A of Compound A At ambient temperature, crystalline Form A of Compound A obtained in Example 14 was added in toluene to reach a 7% m/m concentration. The mixture was stirred at ambient temperature for 8 hours in order to get the polymorphic transition complete. The obtained suspension (slurry) was then filtrated and dried between 20° C. and 70° C. under vacuum in order to get the crystalline Form M of Compound A. The solid was characterized by the X-ray powder diffraction diagram as set out in Example 7.

EXAMPLE 17

Stability Studies of Crystalline Form A of Compound A

For all storage conditions and storage periods, 1.2 g of crystalline Form A of Compound A obtained according to the process of Example 15 were introduced in a specific packaging for post-storage HPLC analysis. Results are as follows:

| Storage Conditions | Packaging | (i) Polymorphic (ii) Chemical stabilities (% m/m)* |
|---|---|---|
| 25° C./60% RH | Polyethylene bag filled in sealed quadruple laminated foil bag | (i) Form A (ii) 98.8% after 24 months of storage |
| 30° C./75% RH | Polyethylene bag filled in sealed quadruple laminated foil bag | (i) Form A (ii) 99.3% after 1 month of storage |
| 40° C./75% RH | Polyethylene bag filled in sealed quadruple laminated foil bag | (i) Form A (ii) 99.5% after 6 months of storage |
| 50° C./75% RH | Polyethylene bag filled in sealed quadruple laminated foil bag | (i) Form A (ii) 99.3% after 1 month of storage |

*drug substance content determined by LC (% m/m)

Crystalline Form A of Compound A remains stable after a 24-month storage period under 25° C./60% RH conditions. Crystalline Form A of Compound A still remains stable towards temperature and humidity after a several months storage period under more severe conditions.

EXAMPLE 18

DSC and TGA Profiles of Compound A, Crystalline Form M

The DSC profile of a sample of Compound A, crystalline Form M (obtained according to any one of the processes of Examples 1 to 6) weighing approximately 3 mg, was recorded at 10° C./minutes from 25° C. to 220° C. in pin-hole pierced aluminium pans under a positive now of nitrogen in a TA Instruments Q2000 Differential Scanning Calorimeter.

The TGA profile of a sample of Compound A, crystalline Form M (obtained according to any one of the processes of Examples 1 to 61, weighing approximately 7.5 mg, was recorded at 10° C./minutes from 25° C. to 220° C. in on open aluminium pan under a positive flow of nitrogen in a TA Instruments Q5000 Thermogravimetric Analyzer.

The DSC and TGA profiles (FIG. 11) show that the crystalline Form M of Compound A is anhydrous and melts at around 148° C.

EXAMPLE 19

Process for Obtaining Crystalline Form $M_H$ of Compound A and X-Ray Powder Diffraction Diagram of the Same A hydrated form of Compound A (called Form $M_H$) was prepared following the maturation of Form M in water at 25° C. Approximately 100 ml of purified water is added to 1 g of Compound A placed in a 100-ml glass vessel. The suspension is matured for 4 days at 30° C. under stirring at a speed of 500 rpm. After 4 days the suspension is filtered under a slight vacuum and the filtrate allowed to dry with the vacuum applied for a further 30 minutes. A white-coloured paste is recovered which, with trituration, is slowly transformed into a while powder. The recovered powder was analyzed by XRPD Subsequent X-ray powder analysis in conjunction with water content analysis indicated that the white powder was the hydrated Form $M_H$.

Recording of the data was carried out in the transmission mode using a PANalytical Empyrean diffractometer with a PIXCel ID detector under the following conditions.

Voltage: 45 kV
Current: 40 mA
Mounting: theta/theta
Anode: copper
K alpha-1 wavelength: 1.54060 Å
K alpha-2 wavelength: 1.54443 Å
K alpha-2/K alpha-1 ratio: 0.5
Measurement mode: continuous from 3° to 55° (Bragg's angle 2 theta) in increments of 0.017°
Measurement time per step: 35.5301 s The X-ray powder diffraction diagram of Form $M_H$ of Compound A is expressed in terms of line position (Bragg's angle 2 theta, expressed in degrees±0.2°) and relative intensity (expressed as a percentage relative to the most intense line) (FIG. 12). The significant lines have been collated in the following table:

| Line No. | Angle 2-theta (degrees) | Interplanar distance (Å) |
| --- | --- | --- |
| 1 | 6.29 | 14.056 |
| 2 | 7.26 | 12.181 |
| 3 | 7.92 | 11.170 |
| 4 | 8.35 | 10.594 |
| 5 | 10.11 | 8.751 |
| 6 | 11.05 | 8.008 |
| 7 | 11.49 | 7.699 |
| 8 | 12.74 | 6.949 |
| 9 | 16.72 | 5.304 |
| 10 | 17.36 | 5.109 |
| 11 | 18.47 | 4.805 |
| 12 | 20.04 | 4.431 |
| 13 | 20.53 | 4.326 |
| 14 | 21.07 | 4.216 |
| 15 | 21.58 | 4.118 |
| 16 | 22.22 | 4.001 |
| 17 | 23.15 | 3.841 |
| 18 | 24.41 | 3.647 |

The water content of the powder was also determined by the coulometric method. The result indicated that the new crystalline solid Form $M_H$ contained a considerable amount of water (29.3%).

EXAMPLE 20

Process for Obtaining Crystalline Form $M_{HD}$ of Compound A and X-Ray Powder Diffraction Diagram of the Same A new diffraction profile was recorded when the hydrate Form $M_H$ was heated at 1° C./min from 25° C. to 100° C. The powder resulting from the thermal treatment was analyzed by XRPD. This new diffraction profile was attributed as Form $M_{HD}$ (i.e. the dehydrated form of hydrated Form M).

Recording of the data was carried out in the transmission mode using a PANalytical Empyrean diffractometer with a PIXCel 1D detector under the following conditions:
Voltage: 45 kV
Current: 40 mA
Mounting: theta/theta
Anode: copper
K alpha-1 wavelength: 1.54060 Å
K alpha-2 wavelength: 1.54443 Å
K alpha-2/K alpha-1 ratio: 0.5
Measurement mode: continuous from 3° to 55° (Bragg's angle 2 theta) in increments of 0.017°
Measurement time per step: 35.5301 s The X-ray powder diffraction diagram of Form $M_{HD}$ of Compound A is expressed in terms of line position (Bragg's angle 2 theta, expressed in degrees±0.2°) and relative intensity (expressed as a percentage relative to the most intense line) (FIG. 13). The significant lines have been collated in the following table:

| Line No. | Angle 2-theta Pos. [°2θ] | Interplanar distance (Å) |
| --- | --- | --- |
| 1 | 6.03 | 14.647 |
| 2 | 8.45 | 10.459 |
| 3 | 10.14 | 8.72 |
| 4 | 10.42 | 8.491 |
| 5 | 11.29 | 7.835 |
| 6 | 11.82 | 7.484 |
| 7 | 13.30 | 6.656 |
| 8 | 15.85 | 5.591 |
| 9 | 17.07 | 5.194 |
| 10 | 17.77 | 4.990 |
| 11 | 18.05 | 4.915 |
| 12 | 18.84 | 4.710 |
| 13 | 19.14 | 4.636 |
| 14 | 20.05 | 4.429 |
| 15 | 21.00 | 4.231 |
| 16 | 21.92 | 4.056 |
| 17 | 22.99 | 3.868 |
| 18 | 27.27 | 3.270 |

The invention claimed is:

1. A crystalline Form M of 2-{[5-{3-Chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl) propanoic acid (Compound A).

2. The crystalline Form M of Compound A according to claim 1 in substantially pure form.

3. The crystalline Form M of Compound A according to claim 1, having an X-ray powder diffraction diagram which exhibits at least the following diffraction lines (Bragg's angle 2 theta, expressed in degrees ±0.2°): 8.94 and 18.24.

4. The crystalline Form M of Compound A according to claim 1, having an X-ray powder diffraction diagram which exhibits at least 4, 5, 6, 7, 8, 9, 10, 11, 12, 13, 14 or all of the following diffraction lines (Bragg's angle 2 theta, expressed in degrees ±0.2°): 6.27; 8.94; 9.09; 12.16; 13.67; 14.75; 15.06; 16.97; 17.22; 17.44; 18.24; 19.16; 19.93; 20.91; and 25.88.

5. The crystalline Form M of Compound A according to claim 4, having an X-ray powder diffraction diagram which exhibits the following diffraction lines (Bragg's angle 2 theta, expressed in degrees ±) 0.2°): 8.94; 13.67; 14.75; 17.22; and 18.24.

6. The crystalline Form M of Compound A according to claim 4, having an X-ray powder diffraction diagram which exhibits the following diffraction lines (Bragg's angle 2 theta, expressed in degrees ±0.2°): 6.27; 8.94; 9.09; 12.16; 13.67; 14.75; 15.06; 16.97; 17.22; 17.44; 18.24; 19.16; 19.93; 20.91; and 25.88.

7. The crystalline Form M of Compound A according to claim 6, having the following X-ray powder diffraction diagram, expressed in terms of line position (Bragg's angle 2 theta in degrees ±0.2°) and interplanar distance d (expressed in Å):

| Line No. | Angle 2-theta (degrees) | Interplanar distance (Å) |
| --- | --- | --- |
| 1 | 6.27 | 14.10 |
| 2 | 8.94 | 9.89 |
| 3 | 9.09 | 9.73 |
| 4 | 12.16 | 7.28 |
| 5 | 13.67 | 6.48 |
| 6 | 14.75 | 6.00 |
| 7 | 15.06 | 5.88 |
| 8 | 16.97 | 5.22 |
| 9 | 17.22 | 5.15 |
| 10 | 17.44 | 5.08 |
| 11 | 18.24 | 4.86 |
| 12 | 19.16 | 4.63 |
| 13 | 19.93 | 4.45 |
| 14 | 20.91 | 4.25 |
| 15 | 25.88 | 3.44. |

8. The crystalline Form M of Compound A according to claim 1, having a solid-state $^{13}$C CP/MAS NMR spectrum which exhibits the following peaks (expressed in ppm ±0.2 ppm): 175.1, 153.7, 134.8, 108.9, 71.4 and 35.1.

9. The crystalline Form M of Compound A according to claim 1, having a solid-state $^{13}$C CP/MAS NMR spectrum which exhibits the following peaks (expressed in ppm #0.2 ppm): 175.1, 168.5, 167.4, 164.6, 162.6, 157.5, 156.3, 153.7, 135.5, 134.8, 130.4, 129.9, 128.4, 126.8, 120.9, 119.9, 118.5, 116.9, 112.5, 111.1, 108.9, 78.7, 71.4, 54.9, 42.1, 35.1 and 18.2.

10. A pharmaceutical composition comprising as active ingredient the crystalline Form M of Compound A according to claim 1 in combination with one or more pharmaceutically acceptable carrier, glidant, diluent, excipient or stabilizer.

11. A method of reducing the symptoms of a condition selected from MCL-1 associated cancers, auto-immune diseases and diseases of the immune system in a subject need thereof, comprising administration of the crystalline Form M of Compound A according to claim 1, alone or in combination with one or more pharmaceutically acceptable excipients.

12. The method according to claim 11, wherein the cancer is selected from bladder cancer, brain cancer, breast cancer, cancer of the uterus, chronic lymphoid leukemias, colorectal cancer, esophagus cancer, liver cancer, lymphoblastic leukemias, acute myeloid leukemia, lymphomas, melanomas, malignant haemopathies, myelomas, ovarian cancer, non-small-cell lung cancer, prostate cancer and small-cell lung cancer.

13. A process for the preparation of the crystalline Form M of Compound A according to claim 1, wherein Compound A is crystallized in a solvent selected from toluene, 2-methyltetrahydrofuran, and a mixture of toluene and methyl tert-butyl ether.

14. The process according to claim 13, wherein the Compound A, from which form M is crystallized, is crystalline Form A of Compound A.

15. The process according to claim 13, wherein the concentration of Compound A in the solvent is between 5 to 15% m/m.

16. The process according to claim 13, wherein the process produces a slurry, which slurry is dried between 20° C. and 80° C.

17. The process according to claim 13, wherein the crystallization is seeded using 0.5% to 5% m/m of crystalline Form M of Compound A.

18. The process according to claim 17, wherein the crystallization is seeded at a temperature between 20° C. and 60° C.

* * * * *

UNITED STATES PATENT AND TRADEMARK OFFICE
CERTIFICATE OF CORRECTION

PATENT NO. : 12,129,261 B2  
APPLICATION NO. : 17/295521  
DATED : October 29, 2024  
INVENTOR(S) : Emilie De Baets et al.

Page 1 of 1

It is certified that error appears in the above-identified patent and that said Letters Patent is hereby corrected as shown below:

In the Claims

Claim 9, Column 23, Line 24: "#" should read -- ± --.

Signed and Sealed this  
Twenty-sixth Day of November, 2024

Katherine Kelly Vidal  
*Director of the United States Patent and Trademark Office*